(12) United States Patent
Dodge et al.

(10) Patent No.: US 6,927,024 B2
(45) Date of Patent: Aug. 9, 2005

(54) PCR ASSAY

(75) Inventors: Anthony H. Dodge, San Mateo, CA (US); Yu-Ju G. Meng, Albany, CA (US); Paul W. Sims, San Mateo, CA (US); Dominick V. Sinicropi, Menlo Park, CA (US); P. Mickey Williams, Half Moon Bay, CA (US); Wai Lee Wong, Los Altos Hills, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/449,204

(22) Filed: Nov. 24, 1999

(65) Prior Publication Data

US 2002/0051974 A1 May 2, 2002

Related U.S. Application Data

(60) Provisional application No. 60/110,259, filed on Nov. 30, 1998.

(51) Int. Cl.[7] .......................... C12Q 1/68; C12P 19/34; C07H 21/04; C07K 16/00
(52) U.S. Cl. .......................... 435/6; 435/7.1; 435/91.2; 435/174; 536/23.1; 530/387.1; 530/391.1
(58) Field of Search .......................... 435/6, 91.2, 7.1, 435/174, 7.2; 536/231; 530/387.1, 391.1

(56) References Cited

U.S. PATENT DOCUMENTS

| | | | |
|---|---|---|---|
| 5,270,163 A | | 12/1993 | Gold et al. |
| 5,475,096 A | * | 12/1995 | Gold et al. .................. 536/26 |
| 5,496,938 A | | 3/1996 | Gold et al. |
| 5,631,146 A | | 5/1997 | Szostak et al. |
| 5,652,107 A | | 7/1997 | Lizardi et al. |
| 5,688,670 A | | 11/1997 | Szostak et al. |
| 5,750,373 A | | 5/1998 | Garrard et al. |
| 5,928,907 A | | 7/1999 | Woudenberg et al. |
| 6,287,765 B1 | * | 9/2001 | Cubicciotti |

FOREIGN PATENT DOCUMENTS

| | | |
|---|---|---|
| WO | WO 96/40991 | 12/1996 |
| WO | WO 97/38134 | 10/1997 |
| WO | WO 98/11210 | 3/1998 |

OTHER PUBLICATIONS

Williams et al "Bioactive and nuclease–resistant L–DNA ligand of vasopressin". Proc. Natl. Acad. Sci. USA Oct. 1997, 94 11285–11290.*
Hendrickson et al. "High sensitivitymultianallyte immunoassay using covalent DNa–labeled natibodies and polymerase chain reaction" Nucleic Acids Research. 1995, 23(3): 522–529.*
Gibson et al. "A novel method for real time quantitative RT–PCR" Genome Methods, 1996, 6:995–1001.*
Kawazoe et al. "Bioassay using a labeled oligonucleotide obtained by in vitro selection" Biotechnology Progress. 1997, 13:873–874.*
Sims, P. et al., "Immunopolymerase Chain Reaction Using Real–Time Polymerase Chain Reaction for Detection", *Analytical Biochemistry*, 28:230–232 (2000).
Williams, K. et al., "Bioactive and nuclease–resistant L–DNA ligand of vasopressin", *Proc. Natl. Acad. Sci. USA*, 94:11285–11290 (Oct. 1997).
Barletta et al., "Lowering the Detection Limits of HIV–1 Viral Load Using Real–Time Immuno–PCR for HIV–1 p24 Antigen", *Am. J. Clin. Pathol.*, 122:20–27 (2004).

(Continued)

*Primary Examiner*—BJ Forman
(74) *Attorney, Agent, or Firm*—Merchant & Gould P.C.

(57) ABSTRACT

An oligonucleotide assay is useful for the detection of target compounds in samples which may contain the target compound.

60 Claims, 9 Drawing Sheets

OTHER PUBLICATIONS

Becker–Andre, M., "Quantitative evaluation of mRNA levels" *Methods in Molecular and Cellular Biology* 2:189–201 (1991).

Chang and Huang, "A modified immuno–polymerase chain reaction for the detection of β–glucuronidase from *Escherichia coli*" *Journal of Immunological Methods* 208(1):35–42 (Oct. 13, 1997).

Charlton et al., "In vivo imaging of inflammation using an aptamer inhibitor of human neutrophil elastase" *Chemistry and Biology* 4(11):809–816 (Nov. 1997).

Conrad et al., "In vitro selection of nucleic acid aptamers that bind proteins" *Methods in Enzymology* 267:336–367 (1996).

Davis et al., "Use of a high affinity DNA ligand in flow cytometry" *Nucleic Acids Research* 24(4):702–706 (Feb. 15, 1996).

Drolet et al., "An enzyme–linked oligonucleotide assay" *Nature Biotechnology* 14(8):1021–1025 (Aug. 1996).

Dutton, G., "Developing PCR tests for real–world commercial applications" *Genetic Engineering News* 18(10):1,12, 30,33 (May 15, 1998).

Ellington and Szostak, "In vitro selection of RNA molecules the bind specific ligands" *Nature* 346(6287):818–822 (Aug. 30, 1990).

Ellington and Szostak, "Selection in vitro of single–stranded DNA molecules that fold into specific ligand–binding structures" *Nature* 355(6363):850–852 (Feb. 27, 1992).

Ellington, A., "RNA selection. Aptamers achieve the desired recognition" *Current Biology* 4(5):427–429 (May 1, 1994).

Fasco et al., "Quantitative RNA–polymerase chain reaction–DNA analysis by capillary electrophoresis and laser––induced fluorescence" *Analytical Biochemistry* 224(1):140–147 (Jan 1, 1995).

Ferre, F., "Quantitative of semi–quantitative PCR: reality versus myth" *PCR Methods & Applications* 2(1):1–9 (Aug. 1992).

Gibson et al., "A novel method for real time quantitative RT–PCR" *Genome Research* 6(10):995–1001 (Oct. 1996).

Green et al., "In vitro genetic analysis: selection and amplification of a rare functional nucleic acids" *Methods: A Companion to Methods in Enzymology* 2(1):75–86 (Feb. 1991).

Griswold, W., "Theoretical analysis of the reaction of multivalent antigen with heterogeneous antibody: a model of soluble phase antibody assays" *Journal of Immunoassay* 8(1):145–171 (1987).

Heid et al., "Real time quantitative PCR" *Genome Research* 6(10):986–994 (Oct. 1996).

Hendrickson et al., "High sensitivity multianalyte immunoassay using covalent DNA–labeled antibodies and polymerase chain reaction" *Nucleic Acids Research* 23(3):522–529 (Feb. 11, 1995).

Hnatowich et al., "Protein labelling via deoxyribonucleic acid hybridization" *Nuclear Medicine Communications* 17(1):66–75 (Jan. 1996).

Joerger et al., "Analyte detection with DNA–labeled antibodies and polymerase chain reaction" *Clinical Chemistry* 41(9):1371–1377 (Sep. 1995).

Kawazoe et al., "Bioassay using a labeled oligonucleotide obtained by in vitro selection" *Biotechnology Progress* 13(6):873–874 Nov.–Dec. 1997).

Kellogg et al., "Quantitation of HIV–1 proviral DNA relative to cellular DNA by the polymerase chain reaction" *Analytical Biochemisrty* 189(2):202–208 (Sep. 1990).

Lentz et al., "Detection of low copy number inversions in mouse genomic DNA with unidirectional PCR primers" *Environmental & Molecular Mutagenesis* 30(3):260–263 (1997).

Lin and Jayasena, "Inhibition of multiple thermostable DNA polymerases by a heterodimeric aptamer" *Journal of Molecular Biology* 271(1):100–111 (Aug. 8, 1997).

Niemeyer et al., "Fluorometric polymerase chain reaction (PCR) enzyme–linked immunosorbent assay for quantification of immuno–PCR products in microplates" *Analytical Biochemistry* 246(1):140–145 (Mar. 1, 1997).

Numata and Matsumoto, "Rapid detection of α–human atrial natriuretic peptide in plasma by a sensitive immuno–PCR sandwich assay" *Clinica Chimica Acta* 259(1–2):169–176 (Mar. 18, 1997).

O'Connor et al., "The dependence of the detection limit of reagent–limited immunoassay on antibody affinity" *Biochemical Society Transactions* 23(2):393s (May 1995).

Pang et al., "High levels of unintegrated HIV–1 DNA in brain tissue of AIDS dementia patients" *Nature* 343(6253):85–89 (Jan. 4, 1990).

Piatak et al., "High levels of HIV–1 in plasma during all stages of infection determined by competitive PCR" *Science* 259(5102):1749–1754 (Mar. 19, 1993).

Piatak et al., "Quantitative competitive polymerase chain reaction for accurate quantitation of HIV DNA and RNA species" *Biotechniques* 14(1):70–81 (Jan. 1993).

Raeymaekers, L., "A commentary on the practical applications of competitive PCR" *Genome Research* 5(1):91–94 (Aug. 1995).

Rasmussen et al., "Quantitative PCR by continuous fluorescence monitoring of a double strand DNA specific binding dye" *Biochemica* 2:8–15 (1998).

Ruzicka et al., "Immuno–PCR with a commercially available avidin system" *Science* 260(5108):698–699 (Apr. 30, 1993).

Sanna et al., "Rapid induction of tumor necrosis factor α in the cerebrospinal fluid after intracerebroventricular injection of lipopolysaccharide revealed by a sensitive capture immuno–PCR assay" *Proc. Natl. Acad. Sci. USA* 92(1):272–275 (Jan. 3, 1995).

Sano et al., "Immuno–PCR: very sensitive antigen detection by means of specific antibody–DNA conjugates" *Science* 258(5079):120–122 (Oct. 2, 1992).

Sperl et al., "Soluble T cell receptors: detection and quantitative assay in fluid phase via ELISA or immuno–PCR" *Journal of Immunological Methods* 186(2):181–194 (Oct. 26, 1995).

Szostak et al., "In vitro genetics" *Trends in Biochemical Sciences* 17(3):89–93 (Mar 1992).

Tuerk and Gold, "Systematic evolution of ligands by exponential enrichment: RNA ligands to bacteriophage T4 DNA polymerase" *Science* 249(4968):505–510 (Aug. 3, 1990).

Williams et al., "Quantitative competitive polymerase chain reaction: analysis of amplified products of the HIV–1 gag gene by capillary electrophoresis with laser–induced fluorescence detection" *Analytical Biochemistry* 236(1):146–152 (Apr. 5, 1996).

Zhou et al., "Universal immuno–PCR for ultra–sensitive target protein detection" *Nucleic Acids Research* 21(25):6038–6039 (Dec. 25, 1993).

* cited by examiner

SEQUENCE LISTING

```
<160> NUMBER OF SEQ ID NOS: 32

<210> SEQ ID NO 1
<211> LENGTH: 80
<212> TYPE: RNA
<213> ORGANISM: artificial sequence
<220> FEATURE:
<223> OTHER INFORMATION: Sequence source:  synthetic

<400> SEQUENCE: 1
gggaauggau ccacaucuac gaauucuuug aagaggguca auccgcgcac          50
guuacguuca cugcagacuu gacgaagcuu                               80

<210> SEQ ID NO 2
<211> LENGTH: 80
<212> TYPE: RNA
<213> ORGANISM: artificial sequence
<220> FEATURE:
<223> OTHER INFORMATION: Sequence source:  synthetic

<400> SEQUENCE: 2
gggaauggau ccacaucuac gaauucggga acagcucuau uccgcgcacg          50
uuugaguuca cugcagacuu gacgaagcuu                               80

<210> SEQ ID NO 3
<211> LENGTH: 80
<212> TYPE: RNA
<213> ORGANISM: artificial sequence
<220> FEATURE:
<223> OTHER INFORMATION: Sequence source:  synthetic

<400> SEQUENCE: 3
gggaauggau ccacaucuac gaauccgcg cacguagguu ggguguaacu           50
gcguuguuca cugcagacuu gacgaagcuu                               80

<210> SEQ ID NO 4
<211> LENGTH: 80
<212> TYPE: RNA
<213> ORGANISM: artificial sequence
<220> FEATURE:
<223> OTHER INFORMATION: Sequence source:  synthetic

<400> SEQUENCE: 4
gggaauggau ccacaucuac gaauccgcg cacguagguu ggguguaacu           50
gcguuguuca cugcagacuu gacgaagcuu                               80

<210> SEQ ID NO 5
<211> LENGTH: 80
```

```
<212> TYPE: RNA
<213> ORGANISM: artificial sequence
<220> FEATURE:
<223> OTHER INFORMATION: Sequence source: synthetic

<400> SEQUENCE: 5
gggaauggau ccacaucuac gaauucaggu ggaaagcaag uuccgcgcac         50
guuaauuuca cugcagacuu gacgaagcuu                              80

<210> SEQ ID NO 6
<211> LENGTH: 80
<212> TYPE: RNA
<213> ORGANISM: artificial sequence
<220> FEATURE:
<223> OTHER INFORMATION: Sequence source: synthetic

<400> SEQUENCE: 6
gggaauggau ccacaucuac gaauccgcg cacgucacgg gccgacacga         50 auagguuca cugcagacuu gacgaagcuu                               80

<210> SEQ ID NO 7
<211> LENGTH: 80
<212> TYPE: RNA
<213> ORGANISM: artificial sequence
<220> FEATURE:
<223> OTHER INFORMATION: Sequence source: synthetic
<220> FEATURE:
<221> NAME/KEY: unsure
<222> LOCATION: 44, 47, 49
<223> OTHER INFORMATION: unknown base

<400> SEQUENCE: 7
gggaauggau ccacaucuac gaauccgcg cgcgcuaacc uugnggngna         50
aguauguuca cugcagacuu gacgaagcuu                              80

<210> SEQ ID NO 8
<211> LENGTH: 80
<212> TYPE: RNA
<213> ORGANISM: artificial sequence
<220> FEATURE:
<223> OTHER INFORMATION: Sequence source: synthetic

<400> SEQUENCE: 8
gggaauggau ccacaucuac gaauucggau auuccgcgca cgucauuuca         50
ucagcuuuca cugcagacuu gacgaagcuu                              80

<210> SEQ ID NO 9
<211> LENGTH: 80
<212> TYPE: RNA
<213> ORGANISM: artificial sequence
<220> FEATURE:
<223> OTHER INFORMATION: Sequence source: synthetic

<400> SEQUENCE: 9
gggaauggau ccacaucuac gaauucaggc agcguagagg guucacucug         50
ccgaguuuca cugcagacuu gacgaagcuu                              80

<210> SEQ ID NO 10
<211> LENGTH: 80
<212> TYPE: RNA
<213> ORGANISM: artificial sequence
<220> FEATURE:
<223> OTHER INFORMATION: Sequence source: synthetic
```

```
<400> SEQUENCE: 10
gggaauggau ccacaucuac gaauucgagg guccgucugc cgagucuugu          50
aacaccuuca cugcagacuu gacgaagcuu                               80

<210> SEQ ID NO 11
<211> LENGTH: 80
<212> TYPE: RNA
<213> ORGANISM: artificial sequence
<220> FEATURE:
<223> OTHER INFORMATION: Sequence source:  synthetic

<400> SEQUENCE: 11
gggaauggau ccacaucuac gaauucgaug gcguuagugg gaaugauucu          50
gccgaguuca cugcagacuu gacgaagcuu                               80

<210> SEQ ID NO 12
<211> LENGTH: 80
<212> TYPE: RNA
<213> ORGANISM: artificial sequence
<220> FEATURE:
<223> OTHER INFORMATION: Sequence source:  synthetic

<400> SEQUENCE: 12
gggaauggau ccacaucuac gaauccguu cugccgagac ugcacgugug           50
cuugaauuca cugcagacuu gacgaagcuu                               80

<210> SEQ ID NO 13
<211> LENGTH: 80
<212> TYPE: RNA
<213> ORGANISM: artificial sequence
<220> FEATURE:
<223> OTHER INFORMATION: Sequence source:  synthetic

<400> SEQUENCE: 13
gggaauggau ccacaucuac gaaucugua agauuggucu ccagacugcc          50
gagcuguuca cugcagacuu gacgaagcuu                               80

<210> SEQ ID NO 14
<211> LENGTH: 77
<212> TYPE: DNA
<213> ORGANISM: artificial seqence
<220> FEATURE:
<221> NAME/KEY: artificial sequence
<222> LOCATION: 1-77
<223> OTHER INFORMATION: Sequence source:  VEGF 49 aptamer

<400> SEQUENCE: 14
gggagctcag aataaacgct caagacccat cgtcaacggt tgagtctgtc          50
ccgttcgaca tgaggcccgg atccggc                                  77

<210> SEQ ID NO 15
<211> LENGTH: 77
<212> TYPE: DNA
<213> ORGANISM: artificial sequence
<220> FEATURE:
<223> OTHER INFORMATION: Sequence source:  VEGF 126 aptamer

<400> SEQUENCE: 15
gggagctcag aataaacgct caaacggttc tgtgtgtgga ctagccgcgg          50
ccgttcgaca tgaggcccgg atccggc                                  77
```

<210> SEQ ID NO 16
<211> LENGTH: 48
<212> TYPE: DNA
<213> ORGANISM: artificial sequence
<220> FEATURE:
<223> OTHER INFORMATION: Sequence source: synthetic primer

<400> SEQUENCE: 16
ccgaagctta atacgactca ctatagggag ctcagaataa acgctcaa         48

<210> SEQ ID NO 17
<211> LENGTH: 24
<212> TYPE: DNA
<213> ORGANISM: artificial sequence
<220> FEATURE:
<223> OTHER INFORMATION: Sequence source: synthetic primer

<400> SEQUENCE: 17
gccggatccg ggcctcatgt cgaa                                   24

<210> SEQ ID NO 18
<211> LENGTH: 18
<212> TYPE: DNA
<213> ORGANISM: artificial sequence
<220> FEATURE:
<223> OTHER INFORMATION: Sequence source: synthetic primer

<400> SEQUENCE: 18
ataaacgctc aagaccca                                          18

<210> SEQ ID NO 19
<211> LENGTH: 14
<212> TYPE: DNA
<213> ORGANISM: artificial sequence
<220> FEATURE:
<223> OTHER INFORMATION: Sequence source: synthetic primer

<400> SEQUENCE: 19
ccgggcctca tgtc                                              14

<210> SEQ ID NO 20
<211> LENGTH: 22
<212> TYPE: DNA
<213> ORGANISM: artificial sequence
<220> FEATURE:
<223> OTHER INFORMATION: Sequence source: synthetic probe

<400> SEQUENCE: 20
cgtcaacggt tgagtctgtc cc                                     22

<210> SEQ ID NO 21
<211> LENGTH: 18
<212> TYPE: DNA
<213> ORGANISM: artificial sequence
<220> FEATURE:
<223> OTHER INFORMATION: Sequence source: synthetic primer

<400> SEQUENCE: 21
agaataaacg ctcaaacg                                          18

<210> SEQ ID NO 22
<211> LENGTH: 15
<212> TYPE: DNA
<213> ORGANISM: artificial sequence
<220> FEATURE:
<223> OTHER INFORMATION: Sequence source: synthetic primer

```
<400> SEQUENCE: 22
gcctcatgtc gaacg                                                    15

<210> SEQ ID NO 23
<211> LENGTH: 18
<212> TYPE: DNA
<213> ORGANISM: artificial sequence
<220> FEATURE:
<223> OTHER INFORMATION: Sequence source:  synthetic probe

<400> SEQUENCE: 23
ccgcggctag tccacaca                                                 18

<210> SEQ ID NO 24
<211> LENGTH: 23
<212> TYPE: DNA
<213> ORGANISM: artificial sequence
<220> FEATURE:
<223> OTHER INFORMATION: Sequence source:  synthetic primer

<400> SEQUENCE: 24
cccagtcacg acgttgtaaa acg                                           23

<210> SEQ ID NO 25
<211> LENGTH: 23
<212> TYPE: DNA
<213> ORGANISM: artificial sequence
<220> FEATURE:
<223> OTHER INFORMATION: Sequence source:  synthetic primer

<400> SEQUENCE: 25
agcggataac aatttcacac agg                                           23

<210> SEQ ID NO 26
<211> LENGTH: 76
<212> TYPE: DNA
<213> ORGANISM: artificial sequence
<220> FEATURE:
<223> OTHER INFORMATION: Sequence source:  synthetic library
<220> FEATURE:
<221> NAME/KEY: unsure
<222> LOCATION: 23-52
<223> OTHER INFORMATION: unknown base

<400> SEQUENCE: 26
gggaatggat ccacatctac gannnnnnnn nnnnnnnnnn nnnnnnnnnn              50
nnttcactgc agacttgacg aagctt                                        76

<210> SEQ ID NO 27
<211> LENGTH: 41
<212> TYPE: DNA
<213> ORGANISM: artificial sequence
<220> FEATURE:
<223> OTHER INFORMATION: Sequence source:  synthetic primer

<400> SEQUENCE: 27
gataatacga ctcactatag ggaatggatc cacatctacg a                       41

<210> SEQ ID NO 28
<211> LENGTH: 24
<212> TYPE: DNA
<213> ORGANISM: artificial sequence
<220> FEATURE:
<223> OTHER INFORMATION: Sequence source:  synthetic primer

<400> SEQUENCE: 28
```

```
aagcttcgtc aagtctgcag tgaa                                          24

<210> SEQ ID NO 29
<211> LENGTH: 71
<212> TYPE: DNA
<213> ORGANISM: Unknown
<220> FEATURE:
<223> OTHER INFORMATION: Sequence source:  woodchuck hepatitis B virus

<400> SEQUENCE: 29
ccaacctcct gtccaccaac tctttcgttg gatgtatctg cggcgtttat             50
gttggttctc ctggactgga a                                            71

<210> SEQ ID NO 30
<211> LENGTH: 20
<212> TYPE: DNA
<213> ORGANISM: artificial sequence
<220> FEATURE:
<223> OTHER INFORMATION: Sequence source:  synthetic primer

<400> SEQUENCE: 30
ccaacctcct gtccaccaac                                              20

<210> SEQ ID NO 31
<211> LENGTH: 23
<212> TYPE: DNA
<213> ORGANISM: artificial sequence
<220> FEATURE:
<223> OTHER INFORMATION: Sequence source:  synthetic primer

<400> SEQUENCE: 31
ttccagtcca ggagaaacca aca                                          23

<210> SEQ ID NO 32
<211> LENGTH: 27
<212> TYPE: DNA
<213> ORGANISM: artificial sequence
<220> FEATURE:
<223> OTHER INFORMATION: Sequence source:  synthetic probe

<400> SEQUENCE: 32
ctttcgttgg atgtatctgc ggcgttt                                      27
```

PCR ASSAY

This application claims the benefit of 60/110,255 filed on Nov. 30, 1998.

FIELD OF THE INVENTION

The invention relates to a method for a novel method for detecting the presence of a target compound, in a sample which may contain the target compound, using a nucleic acid detector molecule, amplification and quantitation or detection of the detector molecule.

BACKGROUND OF THE INVENTION

Numerous assays are known for detecting analytes in a sample. Two general types of analytes are protein analytes and nucleic acid analytes. The technology and assays directed at detecting proteins have historically developed separately and largely independently from the technology and assays directed at detecting nucleic acids. Several reasons exist for this trend in these two fields. Initially, proteins and nucleic acids are chemically distinct and have very different chemical and physical properties. Assays to detect proteins were developed first, due in part to the presence and stability of proteins in the blood, urine, saliva, etc., samples which are readily available, and to the early correlation of physiological condition or disease with the presence proteins. Nucleic acids are generally less stable under assay conditions and are not found readily in free form in body fluids. Assays to detect nucleic acid analytes were developed much later and substantially independently from the protein assays. Assays for nucleic acids have been cumbersome, with low though-put, poor specificity and poor quantitative ability. Currently, protein analytical assays and nucleic acid analytical assays are considered to be two separate fields and practitioners in the two fields do not look to the literature of the other field for guidance in solving problems.

Early protein assays relied on the ability of antibodies to bind to specific protein analytes with sufficiently low dissociation constant (Kd) and with adequate specificity. Antibody capture assays are an easy and convenient screening method. In an antibody capture assay, an antigen is bound to a solid substrate, antibodies are allowed to bind to the antigen and then unbound antibodies are removed by washing. The bound antibodies are then detected using a detector molecule which specifically recognizes the antibody. Most antibody capture assays rely on an indirect method of detecting the antibody. For example, where the antibody is a murine antibody, the detector molecule might be a rabbit anti-mouse antibody which has been labeled with a detectable tag. Conventionally detectable tags have included radioactive isotopes, dyes and enzymes which act on a substrate to produce a detectable molecule, e.g., a chromogen.

In an antigen capture assay, the detection method identifies the presence of an antigen in a sample. In these methods, an antibody is bound to a solid support initially and then the antigen is allowed to react with the antibody to form a complex and the complex is subsequently detected. Alternatively, an antibody-antigen complex may be formed prior to binding of the antibody to a solid phase followed by detection of the complex.

A well known immunoassay is the enzyme-linked immunosorbent assay (ELISA) which when introduced in 1971 started a revolution in diagnostic methods. Conventional ELISA technology is a sandwich assay in which two antibodies or binding proteins simultaneously bind to an antigen or analyte. (Burgess, 1988.) Typically, a capture antibody is bound to a surface and binds to the analyte or antigen in a sample to form an antibody:antigen complex. A detecting antibody capable of binding the antigen or analyte and coupled to an enzyme is then used to form a capture antibody:antigen:detecting antibody sandwich complex and the complex is detected by measuring enzymatic activity of the enzyme bound to the detecting antibody.

Although assays using antibodies are very useful, it is generally accepted that the detection limit of an assay is limited by the Kd of the antibody used as the capture molecule (Griswold, W. (1987) J. Immunoassay 8: 145–171; O'Connor, T., et al. (1995) Biochem. Soc. Trans. 23(2): 393S). In practice, the detection limit of these assays is approximately 1% of the capture antibody Kd. As the concentration of analyte decreases to this sensitivity limit, the low percentage of capture molecules with bound analyte is insufficient to produce a detectable signal to noise ratio. For this reason, antibody based assays using state of the art fluorimetric or chemiluminescent detection systems have a detection limit of about 1 pg/ml (10 e–14 M for an "average" protein of molecular weight 50,000 daltons). See also Tijssen, P., Practice and Theory of Enzyme Immunoassays in Laboratory Techniques in Biochemistry and Molecular Biology, vol. 15, ed. by Burdon, R. H. and van Knippenberg, P. H., Elsevier, N.Y., 1985, pp. 132–136.

The detection of nucleic acid analytes requires different technology. In the mid-1980's, research in DNA technology lead to a method in which DNA could be amplified through a repeated enzymatic amplification process (Saiki et al., 1985; Mullis et al., 1987). The process, later named the polymerase chain reaction (PCR), uses two complementary oligonucleotide sequences (called primers) that flank the region of interest (5' to 3'). The enzymatic process began with a denaturation step in the presence of the primers, then the temperature was lowered to allow primer annealing and Klenow fragment DNA polymerase I was added to extend the primers. Through repeated denaturation, annealing and extension of the desired fragment, exponential amplification of the target DNA was achieved. Many improvements have been made to PCR, but one important change was the incorporation of a DNA polymerase from *Thermus aquaticus* (Taq), a thermophilic bacterium (Saiki et al., 1988). Taq polymerase is a thermostable polymerase and is nearly unaffected by the denaturation steps involved in PCR, an improvement over the previous system where Klenow DNA polymerase I would have to be added to the reaction periodically because the enzyme did not tolerate the denaturation step and lost activity.

In this type of enzymatic reaction, under conditions that allow primers to anneal efficiently, an exponential accumulation or a doubling of the template occurs every cycle. Such amplification allows for extremely low detection levels, some claiming to be able to detect single amplicons in a background of many other DNA molecules (Lentz et al., 1997).

Conventional PCR amplification is not a quantitative detection method, however. During amplification, primer dimers and other extraneous nucleic acids are amplified together with the nucleic acid corresponding to the analyte. These impurities must be separated, usually with gel separation techniques, from the amplified product resulting in possible losses of material. Although methods are known in which the PCR product is measured in the log phase (Kellogg et al., 1990; Pang et al, 1990), these methods require that each sample have equal input amounts of nucleic acid and that each sample amplifies with identical efficiency, and are therefore, not suitable for routine sample analyses. To allow an amount of PCR product to form which is sufficient for later analysis and to avoid the difficulties noted above, quantitative competitive PCR amplification uses an internal control competitor and is stopped only after the log phase of product formation has been completed (Becker-Andre, 1991; Piatak et al., 1993a, b).

In one application of PCR as an amplification system (Sano et al., 1992), an immuno-PCR method was developed that linked a microplate assay for a specific analyte with the amplification power of PCR for detection. The method detected, but did not quantitate, Bovine Serum Albumin (BSA) passively absorbed to an immuno-assay plate. Using an antibody specific for BSA, then bridging a biotin-labeled reporter amplicon with a protein A-streptavidin fusion protein, the assay utilized PCR amplification to detect several hundred molecules of BSA by agarose gel analysis of the reporter amplicon. However, this method could not be applied to biological samples due to the absence of aa specific analyte capture molecule. Others have improved the method by substituting the protein A-streptavidin fusion protein, which was not widely available, with a biotinylated secondary antibody and a streptavidin bridge to bind the biotinylated reporter amplicon (Zhou et al., 1993). The addition of the five assay reagents plus washing, PCR amplification and detection resulted in an assay that was laborious and was subjected to both stoichiometric and disassociation complications (Hendrickson et al., 1995). Another improvement in this assay approach came with the development of a method to covalently link a reporter amplicon to the secondary antibody (Hendrickson et al., 1995; Hnatowich et al., 1996). The direct linkage of the amplicon decreased the reagents used in the assay and the stoichiometric and disassociation complications that can occur. However, these methods still require significant post-PCR manipulations, adding to increased labor and the very real possibility of laboratory contamination.

Sandwich immuno-PCR is a modification of the conventional ELISA format in which the detecting antibody is labeled with a DNA label, and is applicable to the analysis of biological samples. In an early format of an antibody sandwich immuno-PCR, primary antibody was immobilized to a plate and sequentially, the sample, biotinylated detecting antibody, streptavidin, and biotinylated DNA, were added. This format was later improved by the direct conjugation of the DNA to the antibody and replacement of the gel electrophoresis by using labeled primers to generated a PCR product that can be assayed by ELISA (Niemeyer et al., 1996). The amplification ability of PCR provides large amounts of the DNA label which can be detected by various methods, typically gel electrophoresis with conventional staining (T. Sano et al., 1992, *Science*, 258: 120–122). Replication of the antibody-borne DNA label using PCR provides enhanced sensitivity for antigen detection. Immuno-PCR techniques have been extended to the detection of multiple analytes (Joerger et al., 1995; Hendrickson, 1995). While immuno-PCR has provided sensitivities exceeding those of conventional ELISA, purification of the amplified product by gel electrophoresis requires substantial human manipulation and is, therefore, time-consuming. Further, the primers used in the PCR amplification step may dimerize and the dimers are amplified under the PCR conditions leading to side products which compete for PCR amplification. In addition, matrix nucleic acids and other contaminating nucleic acids may be present or introduced and will be amplified by PCR.

Using a primary capture antibody, immuno-PCR methods and reagents are similar to a direct sandwich antigen ELISA, the difference coming at the choice of the detection method. Immuno-PCR methods have been successful and claim to obtain attomole level of sensitivity in some cases, including the detection of the following analytes: tumor necrosis factor $\propto$ (Sanna et al., 1995), $\beta$-galactosidase (Hendrickson et al., 1995), human chorionic gonadotropin, human thyroid stimulating hormone, soluble murine T-cell receptor (Sperl et al., 1995), recombinant hepatitis B surface antigen (Miemeyer et al., 1995), $\alpha$-human atrial natriuretic peptide (Numata et al., 1997) and $\beta$-glucuronidase (Chang et al., 1997).

In immuno-PCR, antigen concentrations are generally determined by post PCR analysis of the reporter amplicon by either gel electrophoresis or PCR-ELISA. Quantitation of the DNA label by analyzing the endpoint PCR product is prone to errors since the rate of product formation decreases after several cycles of logarithmic growth (Ferre, 1992; Raeymakers et al., 1995) and the post PCR sample handling may lead to laboratory contamination. In addition, these methods require multiple steps and washes, during which the antibody:antigen complex may dissociate (Tijssen, P., ibid.).

Another method for amplicon quantitation, e.g. quantitative competitive PCR, uses laser induced capillary electrophoresis techniques to assess fluorescent PCR products (Fasco et al., 1995; Williams et al., 1996). In the context of a immuno-PCR analysis, all of these amplicon quantitation techniques require significant post PCR analysis and induce the possibility of PCR product contamination of the laboratory for following assays because of the handling requirements. Furthermore, these techniques are only able to analyze end-point PCR, PCR that has been stopped at a fixed PCR cycle number (e.g. 25 cycles of PCR). This poses a problem in the dynamic range of amplicon quantitation because only some PCR reactions may be in the log phase of amplification; reactions with high amounts of template will have used all PCR reagents and stopped accumulating amplicon exponentially and reactions with low amounts of template might not have accumulated enough amplicon to be detectable. Therefore, this phenomenon limits the detection range of PCR and can limit the analyte detection range of immuno-PCR assays.

In a further development of PCR technology, real time quantitative PCR has been applied to nucleic acid analytes (Heid et al., 1996). In this method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time. Reverse transcriptase (RT)-real time PCR (RT-PCR) has also been described (Gibson et al., 1996). The Sequence Detection system (ABI Prism, ABD of Perkin Elmer, Foster City, Calif.) uses a 96-well thermal cycler that can monitor fluorescent spectra in each well continuously in the PCR reaction, therefore the accumulation of PCR product can be monitored in 'real time' without the risk of amplicon contamination of the laboratory.

The Sequence Detection system takes advantage of a fluorescence energy theory known as Förster-type energy transfer (Lakowicz et al., 1983). The PCR reaction contains a fluorescently dual-labeled non-extendible probe that binds to the specific target between the PCR primers (FIG. 1*a*).

The probe commonly contains a FAM (6-carboxyfluorescein) on the 5'-end and a TAMRA (6-carboxy-tetramethylrhodamine) on the 3'-end. When the probe is intact, the FAM dye (reporter dye) fluorescence emission is quenched by the proximity of the TAMRA dye (quencher dye) through Förster-type energy transfer. As PCR cycling continues, amplicon is produced and the hybridized probe is cleaved by the use of a polymerase that contains the 5'-3' nuclease activity which chews through the probe, hence the nickname 'TaqMan®' given to the machine. With the cleavage of the probe, the reporter dye is then physically separated from the quencher dye, resulting in an increase in FAM fluorescence because of decreased quenching by TAMRA. The system uses an argon ion laser for fluorescence excitation (488 nm) and a charge-coupled device (CCD) camera to monitor the PCR reactions and collect fluorescence emission over the range of 500 nm to 660 nm for all 96-wells (SDS User's Manual, 1998). Using a algorithm that takes into account the overlapping emission spectra of the dyes used on the machine, the raw fluorescence data can be determined for the reporter, quencher and passive internal reference (ROX, 6-carboxy-X-rhodamine) dyes. The reference dye is used to normalize cycle to cycle fluorescence variations in each well. The Sequence Detection application then calculates a normalized change in reporter fluorescence ($\Delta R_n$) as follows; $\Delta R_n = (\Delta R_n^+) - (\Delta R_n^-)$, where the $\Delta R_n^+$ is the 'reporter's emission fluorescence'/'passive internal reference fluorescence' for that particular PCR cycle and $\Delta R_n^-$ is the 'reporter's emission fluorescence'/passive internal reference 'fluorescence' for a predetermined background period of the PCR reaction (typically cycles 3–15). Plotting the $\Delta R_n$ versus PCR cycle reveals an amplification plot that represents the accumulation of the amplicon in the PCR reaction and cleavage of the probe (FIG. 1b). Using the provided software, the threshold value is either set manually by the user (at a fixed $\Delta R_n$ value) or calculated, typically at 10 standard deviations above the mean of the background period of PCR ($\Delta R_n$). The point on the amplification plot at which a sample's fluorescence intersects the threshold value is referred to as the $C_t$ value (PCR Cycle threshold) for that sample. Relative amounts of PCR product are compared among PCR reactions using the calculated $C_t$ value. Using the Sequence Detection system, DNA and RNA have been successfully used for quantitative PCR (Heid et al., 1996) and rt-PCR (Gibson et al., 1996).

Nucleic acids have also been used as detector molecules in assays. The idea of "in vitro genetics" has been used to describe the isolation of binding nucleic acid ligands (Szostak et al., 1992). In general, the method involves taking a pool of very diverse nucleic acid sequences (typically degenerate oligonucleotides), introducing these sequences to a target and separating the bound sequences from the unbound sequences. The separation of the bound sequences results in a new pool of oligonucleotides that have been maturated by their preference to interact with the target, a type of genetic selection performed on the lab bench.

Nucleic acid and protein interactions in the cell are not uncommon occurrences. It is known that nucleic acids can fold to form secondary and tertiary structures and that these structures are important for binding interactions with proteins (Wyatt et al., 1989). The maturation of nucleic acid-protein binding interactions has been examined in vitro by varying the sequence of nucleic acid ligands (Tuerk et al., 1990). A technique known as SELEX (Systematic Evolution of Ligands by EXponential enrichment) is used to isolate novel nucleic acid ligands to a target of choice. These ligands were referred to as aptamers. The Greek root 'apta', meaning "to fit", suggests a method for which the nucleic acid may fold and fit into pockets on target molecules. See U.S. Pat. No. 5,652,107; U.S. Pat. No. 5,631,146; U.S. Pat. No. 5,688,670; U.S. Pat. No. 5,652,107; A. D. (Ellington et al., 1992; Ellington et al., 1990; Greene et al., 1991).

The initial development of SELEX focused on a known protein-RNA interaction between Bacteriophage T4-DNA polymerase and a mRNA translational repressor. A well-characterized hairpin that presented a specific eight nucleic acid loop region was involved in the interaction with the polymerase (Andrake et al., 1988). The eight bases in this loop region were completely randomized ($4^8$=65,536 fold complexity) by synthesis on a nucleic acid synthesizer. Specific PCR primer regions were designed to flank the entire sequence for ease in amplification. The primer region also incorporated a bacteriophage T7 promoter so RNA could be easily transcribed from the DNA template. The RNA library, containing the 8-base random region, was mixed with the polymerase and protein-RNA complexes were separated through selective binding to a nitrocellulose filter. The nitrocellulose filters have a higher affinity for proteins than for nucleic acids, therefore capturing the protein and it's associated RNA ligand. The bound RNA was then eluted and rt-PCR performed with the primer set described above. A new matured RNA pool could then be in vitro transcribed from the resulting T7-promoter containing DNA template, completing one cycle of the selection. With repeated cycles of the binding and separation procedure, the random RNA pool was eventually maturated to contain primarily two sequences; one sequence that was identical to the natural ligand found to bind the polymerase, and the other contained a four base difference from the natural ligand.

The power of maturing nucleic acid ligand pools in the SELEX procedure involves separating ligand-target complexes from free nucleic acid sequences. In the selection described above, a membrane that has a higher affinity for protein than RNA was used to create a new matured pool biased for sequences that interact with the protein. Maturation of the selection pool is accelerated by creating competition among the diverse RNA ligands in the pool. By lowering the target concentration, a situation is created where the binding sites are limited. The competition for these binding sites promotes higher affinity ligand selection. An unfortunate problem in some selections is the maturation of non-specific ligands, or ligands that bind to the nitrocellulose filter or other material in the selection procedure. One method used to avoid such ligands involves the use of carrier nucleic acid that cannot be extended by the selection PCR primer set (such as tRNA). Other methods of selection involve alternative procedures to separate ligand-target complexes, such as; affinity column binding, gel-shift assays and immuno-assay capture.

The design of a nucleic acid library involves three main considerations; minimizing amplification artifacts (resulting from miss priming), amount of randomness and length of the random region (Conrad et al., 1996). In designing a PCR amplification system, primer design is important to optimize the amplification of the specific amplicon of choice and to minimize non-specific amplification of other products by miss priming (either to amplicons of non-interest or primer-primer annealing). Primer design is also important in aptamer library design because of the large number of PCR cycles that are performed. A typical SELEX round will include 12–25 PCR cycles and a SELEX selection might include as much as 15 rounds, resulting in over 200 cycles of PCR on the selection pool. It is clear that miss primed PCR artifacts will accumulate in the selection pool that is subjected to such a large amount of PCR cycling. The amount of randomness can play an important role in the selection library if the study protein has a known nucleic acid sequence (such as the T4-DNA polymerase selection above). These libraries can be completely randomized in certain regions (keeping other wild-type sequence intact for secondary structure), or the wild-type sequences can be "doped" to contain a higher percentage of natural bases and a lower percentage of random bases (e.g. 70% G's and 10% A, C or T). Finally, the length of the random region can be varied over a wide range when using proteins that have known nucleic acid interactions. When selecting aptamers with proteins that have no known natural nucleic acid ligands, completely randomized libraries can be used, although the length must be considered. In longer completely randomized pools, greater secondary structure can be obtained because more bases are available. In shorter randomized pools, simpler secondary structure is obtained but a greater representation of all sequence possibilities is achieved (because of the physical limitation in the amount of DNA/RNA that one can select for in the first round). Ellington et al, 1994.

Since the original SELEX experiments, many nucleic acid ligands have been selected to a large variety of targets. Many proteins that normally bind nucleic acids have been shown to be good candidates for these SELEX selections. The designs of such selections have ranged from randomizing only the known binding region (T4 DNA Polymerase) to selections on completely randomized libraries. Other examples include; bacteriophage R17 coat protein (Schneider et al., 1992), E. Coli rho factor (Schneider et al., 1993), E. Coli ribosomal protein S1 (Ringquist et al., 1995) (and other S1 containing proteins, such as 30S particles and Qβ replicase (Brown et al., 1995)), phenylalanyl-tRNA synthetase (Peterson et al., 1993; Peterson et al., 1994), autoimmune antibodies that recognize RNA (Tsai et al., 1992), E2F transcription factor (Ishizaki et al., 1996) and various HIV associated proteins (Tuerk et al., 1993a; Giver et al., 1993; Tuerk et al., 1993b; Allen et al., 1995).

Aptamer selections have also been performed with proteins that were not known to bind to nucleic acids. Thrombin was one of the first candidates and its highest affinity aptamers were shown to be able to block thrombin's ability to cleave fibrinogen to fibrin (Bock et al., 1992; Kubik et al., 1994). Selections have also been carried out on many classes of proteins, including; growth factors (nerve growth factor (Binkley et al., 1995), basic fibroblast growth factor (Jellinek et al., 1993) and vascular endothelial growth factor (Jellinek et al., 1994)), antibodies (antibodies that bind to nuclear antigens (Tsai et al., 1992), insulin receptor (Doudna et al., 1995) and IgE class antibodies (Wiegand et al., 1996)), small molecules (cyanocobalamin (Lorsch et al., 1994), theophylline (Jenison et al., 1994), ATP (Sassanfer et al., 1993), GDP/GMP (Connell et al., 1994), chloroaromatics (Bruno et al., 1997), S-adenosyl methionine (Burke et al., 1997) and a panel of dyes (Ellingtion et al., 1990)) and a variety of other proteins (human thyroid stimulating hormone (Lin et al., 1996), human elastase (Bless et al., 1997), L-selectin (Hicke et al., 1996), protein kinase C (Conrad et al., 1994), Taq DNA polymerase (Dang et al., 1996) and reverse transcriptases, including; AMV (Chen et al., 1994), MMLV (Chen et al., 1994) and FIV (Chen et al., 1996).

The aptamers to the various reverse transcriptases demonstrate the specificity they can acquire. These aptamers did not share sequence motifs, except for the fact that they seem to interact through a series of "A" ribonucleotide bases. When cross tested for binding, the specific ligands did not cross-react with the other evolutionarily closely related transcriptases (Chen et al., 1994; Chen et al., 1996). Another example of specificity involves the RNA ligands to protein kinase C βII form (Conrad et al., 1994). The highest affinity aptamers showed a greater affinity for the βII form (by 1 order of magnitude via $IC_{50}$ binding curve) when binding was compared to the alternatively spliced βI form of protein kinase C, even though they have only a 23 residue difference at the protein level. These aptamers also showed no apparent inhibition to other protein kinase C isozymes (α and ε forms).

The fact that one can generate novel nucleic acid ligands to a large variety of proteins led to the use of aptamers as an alternative to monoclonal and polyclonal antibody production for therapeutic and diagnostic uses. Diagnostic approaches using aptamers in place of antibodies have been evaluated. Aptamers to DNA polymerases have been used in hot start PCR to detect low copy number of the desired amplicon (Lin et al., 1997). Using an aptamer to block polymerase activity at low temperatures in PCR minimizes artifactual amplification and increases PCR sensitivity. Aptamers have also been used as a tool in assay development. An aptamer to neutrophil elastase was fluorescein labeled and used in a flow cytometry assay to determine elastase concentrations (Davis et al., 1996). The same aptamer was also used in an in vivo diagnostic imaging model of an inflamed rat lung (Charlton et al., 1997). Another aptamer to reactive green 19 (RG19) was also fluorescein labeled and used in a semi-quantitative bioassay for RG19 (Kawazoe et al., 1997). An immuno-assay using an aptamer detection reagent was also developed using a fluorescein labeled aptamer to VEGF (Drolet et al., 1996). The indirect immunoassay format was used for the quantitation of VEGF protein using a fluorescent substrate detection system.

In the enzyme-linked oligonucleotide assay (ELONA), one or more of the antibody reagents is replaced with an oligonucleotide sequence which specifically binds to the antigen. A specifically binding oligonucleotide sequence can be obtained by the in vitro selection of nucleic acid molecules which specifically bind to a target molecule using, for example, the SELEX method developed by L. Gold et al. (See Drolet, 1996). U.S. Pat. No. 5,472,841; U.S. Pat. No. 5,580,737; U.S. Pat. No. 5,660,985; U.S. Pat. No. 5,683,867; U.S. Pat. No. 5,476,766; U.S. Pat. No. 5,496,938; U.S. Pat. No. 5,527,894; U.S. Pat. No. 5,595,877; U.S. Pat. No. 5,637,461; U.S. Pat. No. 5,696,248; U.S. Pat. No. 5,670,637; U.S. Pat. No. 5,654,151; U.S. Pat. No. 5,693,502; U.S. Pat. No. 5,668,264; U.S. Pat. No. 5,674,685; U.S. Pat. No. 5,712,375; U.S. Pat. No. 5,688,935; U.S. Pat. No. 5,705,337; U.S. Pat. No. 5,622,828; U.S. Pat. No. 5,641,629; U.S. Pat. No. 5,629,155; U.S. Pat. No. 5,686,592; U.S. Pat. No. 5,637,459; U.S. Pat. No. 5,503,978; U.S. Pat. No. 5,587,468; U.S. Pat. No. 5,637,682; U.S. Pat. No. 5,648,214; U.S. Pat. No. 5,567,588; U.S. Pat. No. 5,707,796; U.S. Pat. No. 5,635,615; etc. WO 96/40991 and WO 97/38134 describe enzyme-linked oligonucleotide assays in which the capture antibody or the detecting antibody of a sandwich assay is replaced with a nucleic acid ligand. Generally, detection of the antigen:capture molecule complex is accomplished using a conventional enzyme-linked detecting antibody. Labeling of the oligonucleotide with a reporter enzyme, however, requires additional chemical synthesis steps and additional labor, difficulties also associated with assays which use antibody reagents as described above.

WO 96/40991 and WO 97/38134 also mention an embodiment in which the detection system is PCR amplification of a nucleic acid ligand which is part of the capture molecule:target molecule:detector molecule complex. These references suggest that the PCR primers used for amplification may contain reporter molecules such as enzymes, biotins, etc. Simple PCR amplification of a nucleic acid ligand provides additional quantities of the ligand, but has the disadvantage of requiring further separation steps to distinguish between the amplified ligand of interest and amplified nucleic acid impurities and primer dimers. Traditional gel separation requires intensive manual labor. Further, replicate experiments are required for statistical analysis and require additional time and labor. These problems exist for both DNA ligands and RNA ligands used in these oligonucleotide assays. The use of labeled primers allows detection of the PCR product, but does not overcome the problems of impurity and primer dimer amplification and is, therefore, not quantitative.

Despite these advances, a need continues to exist for a diagnostic method having improved sensitivity, improved dynamic range and less human manipulation in order to more rapidly analyze samples for the presence of and for the amount of a target antigen. Moreover, assays that use antibodies as capture reagents have detection limits that are approximately 1% of the antibody Kd (1 µg/ml for the highest affinity antibodies); however, a need exists for more sensitive assays of therapeutic and diagnostic analytes.

SUMMARY OF THE INVENTION

Accordingly, one object of the present invention is to provide a quantitative method for detecting the presence and/or the amount of a target compound in a sample where the method has equal or improved sensitivity to conventional methods, has improved dynamic range, has improved resistance to contamination, has improved detection and which requires fewer human manipulation steps.

These and other objects which will become apparent in the course of the following description of exemplary embodiments have been achieved by the present method for detecting the presence of a target compound in a sample which may contain the target compound, where the method uses the following steps:

(a) exposing a sample, which may contain or is suspected of containing the target compound, to a capture molecule capable of binding to the target molecule to form a capture molecule:target molecule complex;

(b) adding to the capture molecule:target molecule complex, a detector molecule containing a nucleic acid moiety and capable of specifically binding to the target molecule; and (c) amplifying the nucleic acid moiety by PCR amplification, and (d) quantitating or detecting the PCR amplified nucleic acid moiety using a detectable non-primer probe capable of binding to the nucleic acid moiety.

The method of the invention is an improvement over conventional immuno-PCR in which an antibody nucleic acid label is amplified with PCR, since such amplification is not itself a detection method and the subsequent gel electrophoresis is both not quantitative and requires many product manipulation steps. The method of the invention is also an improvement over conventional ELONA assays which use aptamers to replace antibodies as detector assay reagents and which may use conventional PCR amplification prior to detection. In the method of the invention, the capture molecule may be an antibody, phage antibody, aptamer or other receptor or binding partner for the analyte of interest.

The detector molecule may be either a nucleic acid labeled antibody or an aptamer capable of binding to the target molecule. Quantification is achieved by detecting the amplified nucleic acid (nucleic acid moiety on the labeled antibody or aptamer) with a detectable non-primer probe capable of binding to the amplified nucleic acid, preferably in real time.

The invention, therefore, provides improvements in quantitation and sensitivity over immuno-PCR and ELONA assays which have been used for protein analytes, by utilizing a PCR amplification and quantification technique used only for application to the real time detection of nucleic acids. The invention also provides improvements over conventional ELISA assays in sensitivity.

The use of non-primer probes, preferably with real time analysis, e.g., the TaqMan® system, in an aptamer-PCR or an immuno-PCR assay as in the invention, overcomes the shortcomings of prior art processes discuss above. Since the PCR reaction products are not subjected to post-PCR manipulations, the risk of product contamination in assays is significantly lowered. Monitoring the PCR reaction in 'real time' allows the collection of data across many cycles (e.g. cycle 1–50) instead of at an end-point PCR stage, as in conventional immuno-PCR (e.g. cycle 25 only), therefore allowing for a greater range of detectable amplicon. The method of the invention can detect the target molecule at a concentration of less than $1.0 \times 10^{-12}$ grams/mL, generally about $1.0 \times 10^{-15}$ to about $1.0 \times 10^{-8}$ grams/mL.

DETAILED DESCRIPTION OF THE PREFERRED EMBODIMENTS

Figure 1A:
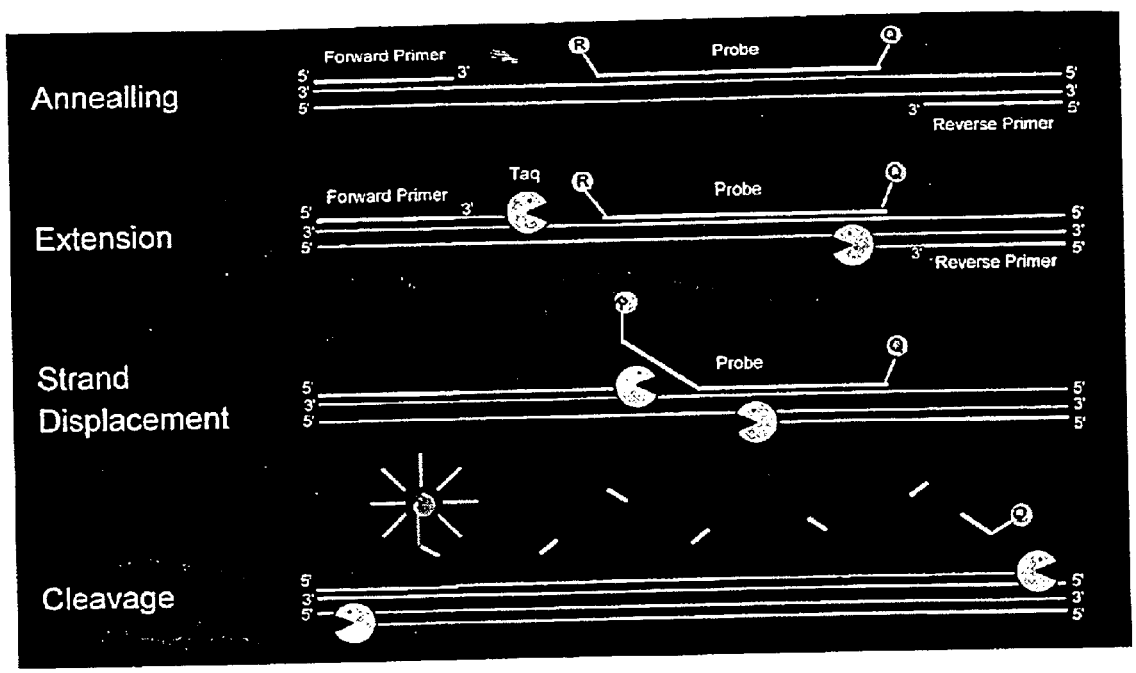
FIG. 1a illustrates the use of a non-primer dual-labeled probe in the method of the invention. A dual-labeled probe binds to the target and is cleaved during PCR extension, releasing the fluorescent dye.
Figure 1B:
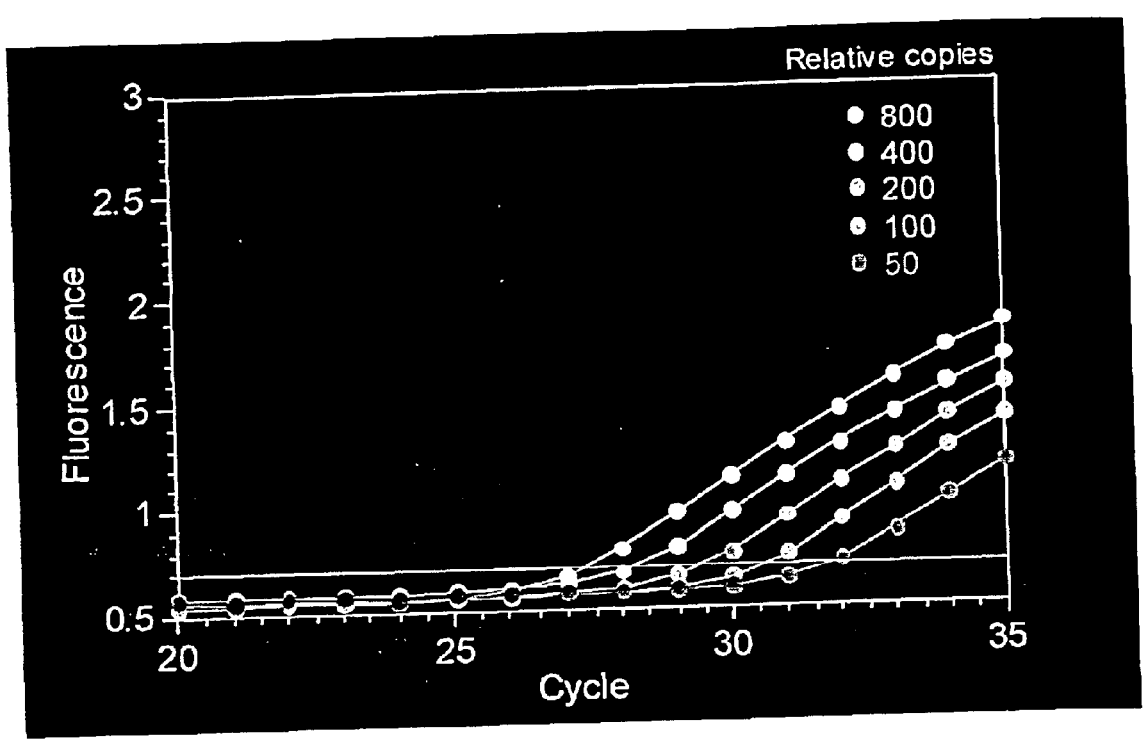
FIG. 1b illustrates fluorescent data collected during the method. As the PCR cycle number increases, and there is a target present, increased amounts of probe are cleaved and an increase in fluorescence can be monitored. The cycle number where the fluorescence value crosses a threshold, value (horizontal line) is called the threshold cycle (Ct). Multiple curves are shown for different initial copies of the target.
Figure 2A:
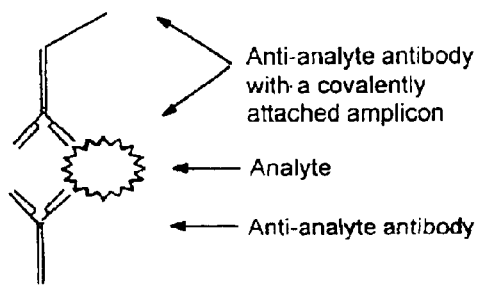
FIG. 2 shows a comparison of conventional immuno-PCR versus the method of the invention using an aptamer as the detecting molecule. Immuno-PCR (FIG. 2a) uses an antibody covalently attached to an amplicon as a detection reagent. The aptamer-PCR (FIG. 2b) has a detection reagent that is both a binding reagent and PCR amplicon in one.
Figure 2B:
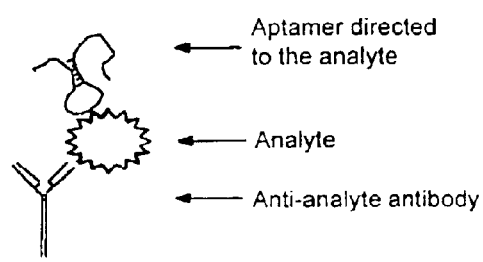

In the method of the invention, the presence of a target compound in a sample which may contain the target compound is detected and may be quantitated by exposing the sample which may contain the target compound to a capture molecule capable of binding the target compound to form a capture molecule:target molecule complex. The presence of the target in a sample can be determined without further quantitating the amount of the target in the sample, if detection only is desired. Detection is achieved by observing a detectable signal from the detectable non-primer probe used in the method. Quantitation is achieved using the detectable non-primer probe and a calibration standard, preferably using real time PCR methods.

The term "capture molecule" as used herein means any molecule or target binding fragment thereof capable of specifically binding to the target compound so as to form a capture molecule:target molecule complex. In this context, "specifically binding" means that the capture molecule binds to the target molecule based on recognition of a binding region or epitope on the target molecule. The capture molecule preferably recognizes and binds to the target molecule with a higher binding affinity than it binds to other compounds in the sample. Preferably, the capture molecule uniquely recognizes and binds to the target molecule.

Typically, the capture molecule will be an antibody, preferably a monoclonal antibody, which immunologically binds to the target compound at a specific determinant or epitope. The term "antibody" is used in the broadest sense and specifically covers monoclonal antibodies as well as antibody fragments (e.g., Fab, F(ab')$_2$, scFv, Fv diabodies and linear antibodies), so long as they exhibit the desired binding activity. For a review of sFv see (Pluckthun, 1994). Diabodies are described more fully in, for example, EP 404,097; WO 93/11161; and (Hollinger et al., 1993). Linear antibodies are described in (Zapata et al, 1995).

The preparation of monoclonal antibodies specific for a target compound is well known and described, for example, in (Harlow and Lane, eds., 1988). The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by (Kohler & Milstein, 1975) or may be made by recombinant DNA methods (see, e.g., U.S. Pat. No. 4,816,567 (Cabilly et al)).

The monoclonal antibodies herein specifically include "chimeric" antibodies (U.S. Pat. No. 4,816,567 (Cabilly et al.); and (Morrison et al., 1984); and humanized antibodies (Jones et al., 1986); (Reichmann et al., 1988); and (Presta, 1992).

The capture molecule may also be a high-affinity nucleic acid ligand which binds to the target molecule, e.g. an aptamer. The term "nucleic acid ligand" as used herein means a nucleic acid, including naturally occurring and non-naturally occurring nucleic acids, having a specific binding affinity for the target molecule. Nucleic acid ligands may be identified and prepared using the SELEX method described in U.S. Pat. No. 5,270,163; U.S. Pat. No. 5,475, 096; U.S. Pat. No. 5,496,938; WO 96/40991; and WO 97/38134, for example. The nucleic acid ligand may be DNA or RNA.

The capture molecule may also be a binding protein, receptor or extracellular domain (ECD) thereof capable of forming a binding complex with a ligand, typically a polypeptide or glycopeptide ligand. In one embodiment, the binding protein is a cytokine superfamily receptor or receptor ECD and the target compound is a cytokine.

"Cytokine superfamily receptors", which can be used as the capture molecule, are a group of closely related glycoprotein cell surface receptors that share considerable homology including frequently a WSXWS domain and are generally classified as members of the cytokine receptor superfamily (see e.g. (Nicola et al., 1991) and (Skoda et al., 1993)). Generally, these receptors are interleukins (IL) or colony-stimulating factors (CSF). Members of the superfamily include, but are not limited to, receptors for: IL-2 (beta and gamma chains) (Hatakeyama et al., 1989); (Takeshita et al., 1991); IL-3 (Itoh et al., 1990); (Gorman et al., 1990); Kitamura et al., 1991a); (Kitamura et al., 1991b); IL-4 (Mosley et al., 1989); IL-5 (Takakiet al., 1990); (Tavernier et al., 1991); IL-6 (Yamasaki et al., 1988); (Hibi et al., 1990); IL-7 (Goodwin et al. 1990); IL-9 (Renault et al., 1992); granulocyte-macrophage colony-stimulating factor (GM-CSF) (Gearing et al., 1991); (Hayashida et al., 1990) granulocyte colony-stimulating factor (G-CSF) (Fukunaga et al., 1990a); (Fukunaga et al., 1990b); (Larsen et al., 1990); EPO (D'Andrea et al., 1989); (Jones et al., 1990) Leukemia inhibitory factor (LIF) (Gearing et al., 1991); oncostatin M (OSM) (Rose et al., 1991); and also receptors for prolactin (Boutin et al., 1988); (Edery et al., 1989); growth hormone (GH) (Leung et al., 1987); ciliary neurotrophic factor (CNTF) (Davis et al., 1991); c-Mpl (M. Souyri et al, 1990); (I. Vigon et al., 1992).

In still another embodiment, the capture molecule is a phage-antibody. Antibodies and antibody fragments may be displayed on the surface of a filamentous bacteriophage as described in U.S. Pat. No. 5,750,373, for example and the references cited therein. See also EP 844306; U.S. Pat. No. 5,702,892; U.S. Pat. No. 5,658,727; WO 97/09436; U.S. Pat. No. 5,723,287; U.S. Pat. No. 5,565,332; and U.S. Pat. No. 5,733,743.

The "detector molecule" may be an antibody labeled with a DNA label or may be a high-affinity nucleic acid ligand, which binds to the target molecule. The detector antibody may be labeled with a DNA label using techniques known for use in conventional immuno-PCR, for example, by crosslinking with Sulfo-SMCC (Pierce, Rockford, Ill.). The term "nucleic acid ligand" as used herein means a nucleic acid, including naturally occurring and non-naturally occurring nucleic acids, having a specific binding affinity for the target molecule. Nucleic acid ligands may be identified and prepared using the SELEX method described in U.S. Pat. No. 5,270,163; U.S. Pat. No. 5,475,096; U.S. Pat. No. 5,496,938; WO 96/40991; and WO 97/38134, for example. The nucleic acid ligand may be DNA or RNA. In its most basic form, the SELEX process has the following steps:

1) A candidate mixture of nucleic acids of differing sequence is prepared. The candidate mixture generally include regions of fixed sequences (i.e., each of the members of the candidate mixture contains the same sequences in the same location) and regions of randomized sequences. The fixed sequence regions are selected either (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with a lesser affinity to the target. Because only a small number of sequences corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The "target molecule" may be any 3-dimensional chemical compound that binds to the capture molecule. The target compound will generally be a protein, carbohydrate or lipid derived from a biological source such as bacterial, fungal, viral, plant or animal samples. The samples may include blood, plasma, serum, sputum, urine, semen, cerebrospinal fluid, bronchial aspirate, organ tissues, etc. Additionally, however, the target compound may be a smaller organic compound such as a drug, drug-metabolite, dye or other small molecule present in the sample. Preferably, the small molecule is an organic target compound having a molecular weight of about at least 100 and up to about 1,000 grams/mole, more preferably about 200 to about 700 grams/mole. When small molecules are the target compound, it is preferred to use nucleic ligands as the capture molecule. A preferred group of target molecules are cytokines.

"Cytokine" is a generic term for proteins released by one cell population which act on another cell as intercellular mediators. Examples of such cytokines are lymphokines, monokines, and traditional polypeptide hormones. Included among the cytokines are growth hormone, insulin-like growth factors, human growth hormone (hGH), N-methionyl human growth hormone, bovine growth hormone, parathyroid hormone, thyroxine, insulin, proinsulin, relaxin, prorelaxin, glycoprotein hormones such as follicle stimulating hormone (FSH), thyroid stimulating hormone (TSH), and leutinizing hormone (LH), hematopoietic growth factor, hepatic growth factor (HGF), fibroblast growth factor, prolactin, placental lactogen, tumor necrosis factor-alpha (TNF-alpha and TNF-beta), mullerian-inhibiting substance, mouse gonadotropin-associated peptide, inhibin, activin, vascular endothelial growth factor (VEGF), integrin, nerve growth factors such as NGF-beta, platelet-growth factor, transforming growth factors (TGFs) such as TGF-alpha and TGF-beta, insulin-like growth factor-I and -II, erythropoietin (EPO), osteoinductive factors, interferons such as interferon-alpha, -beta, and -gamma, colony stimulating factors (CSFs) such as macrophage-CSF (M-CSF), granulocyte-macrophage-CSF (GM-CSF), and granulocyte-CSF (G-CSF), thrombopoietin (TPO), interleukins (IL's) such as IL-1, IL-1alpha, IL-2, IL-3, IL-4, IL-5, IL-6, IL-7, IL-8, IL-9, IL-11, IL-12 and other polypeptide factors including neurturin (NTN), LIF, SCF, and kit-ligand. As used herein the foregoing terms are meant to include proteins from natural sources or from recombinant cell culture. Similarly, the terms are intended to include biologically active equivalents; e.g., differing in amino acid sequence by one or more amino acids or in type or extent of glycosylation.

The capture molecule may be attached to a solid support before or after forming the capture molecule:target molecule complex. Specific capture molecules, e.g. antibodies or aptamers, are prepared as described above and purified using conventional separation techniques. The capture molecules are then attached to solid supports using passive absorbance or other conventional (e.g., chemical) techniques for attaching proteins to solid supports. In a preferred embodiment, the solid support is coated with one member of a known binding pair, e.g. streptavidin, and the capture molecule is labeled with the other member of the binding pair, e.g. biotin. The biotin labeled capture molecule:target molecule complex or the capture molecule:target molecule:detector molecule ternary complex may be formed in solution phase and captured by the streptavidin coated support. In a particularly preferred form of this embodiment, the support is a streptavidin coated PCR tube and the detector molecule is either an aptamer or a DNA labeled antibody. This procedure reduces the number of washing steps, preferably to a single washing step, and does not require handling of the PCR product when used together with real time PCR.

Other suitable binding pairs which can be used in this embodiment include any known epitope tags and binding partners therefor, generally antibodies which recognize the tag. The term "epitope tagged" refers to an capture molecule fused to an "epitope tag". The epitope tag polypeptide has enough residues to provide an epitope against which an antibody thereagainst can be made, yet is short enough such that it does not interfere with activity of the capture molecule. The epitope tag preferably is sufficiently unique so that the antibody thereagainst does not substantially cross-react with other epitopes. Suitable tag polypeptides generally have at least 6 amino acid residues and usually between about 8–50 amino acid residues (preferably between about 9–30 residues). Examples include the flu HA tag polypeptide and its antibody 12CA5 (Field et al. *Mol. Cell. Biol.* 8: 2159–2165 (1988)); the c-myc tag and the 8F9, 3C7, 6E10, G4, B7 and 9E10 antibodies thereto (Evan et al., *Mol. Cell. Biol.* 5(12): 3610–3616 (1985)); and the Herpes Simplex virus glycoprotein D (gD) tag and its antibody (Paborsky et al., *Protein Engineering* 3(6): 547–553 (1990)), digoxigenin/anti-digoxigenin antibody, FITC/anti-FITC antibody, $His_6$/Ni columns, Protein A/antibody Fc regions, etc. In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Any suitable solid support is useful in the method of the present invention. Suitable solid supports include membranes, charged paper, nylon, beads, polystryrene ELISA plates, PCR tubes (Numata et al, 1997), V-bottom polycarbonate plates (Chang et al, 1997), etc. Suitable membranes include nitrocellulose membranes and polyvinylidine difluoride membranes. In a preferred embodiment, the capture molecule is bound to a polymer bead, tube or plate, for example a conventional polycarbonate plate.

The capture molecule (alone or attached to the solid support) is exposed to a sample which may contain the target compound under conditions suitable for complex formation and, if target compound is present, the capture molecule binds to the target molecule forming a capture molecule-:target molecule complex. To avoid nonspecific binding of the target molecule to a solid support, the solid support is generally treated to block nonspecific binding sites prior to exposing the sample to the capture molecule. Common blocking agents include dilute protein solutions (about 3–5%), for example bovine serum albumin (BSA), and nonionic detergents (polyvinyl pyrrolidone, PVP-40) and TWEEN 20. Typically, the capture molecule bound to a solid support is incubated under conditions sufficient to block nonspecific binding sites. In direct binding, blocking occurs by incubating the solid support having the capture molecule bound thereto in a solution of the blocking agent at about room temperature (or other suitable temperature) for several hours (2–20 hours) with agitation according to known methods. The blocking solution is then generally washed from the solid support to remove remaining blocking agent.

The sample to be tested for the presence of the target molecule is then placed in contact with the capture molecule under conditions sufficient to allow the formation of a capture molecule:target molecule complex. Optionally, the sample may be diluted as needed prior to contact with the capture molecule. In most cases, the target sample will be an aqueous sample, although other sample media are suitable as long as the media allows formation of the desired binding complex. Ordinary optimization of assay parameters is within the skill of the practitioner in this field and will generally involve optimizing ionic strength, divalent metal ion concentration, pH, etc. Optimization is generally performed for each different target. The assay is preferably run under the same conditions as used for aptamer selection, when an aptamer is used as the capture molecule or the detection molecule.

After a time sufficient to allow formation of the capture molecule:target molecule complex, unbound or remaining sample is removed from the complex, generally by washing. Typically, the complex is washed with 1–3 volumes of water or suitable buffer.

The detector molecule is placed in contact with the capture molecule:target molecule complex to form a capture molecule:target molecule:detector molecule ternary complex. The detector molecule is generally dissolved in an aqueous solution, preferably an aqueous buffer solution and contacted with the capture molecule:target molecule complex. Suitable buffers are those well known in the art for buffering antibody and nucleic acid ligand molecules, and include known buffers used in conventional ELISA, PCR, immuno-PCR and ELONA assays. After a time sufficient to allow formation of the desired ternary complex, unbound detector molecule is removed from the complex, preferably by washing with water or buffer. The ternary complex is then ready for amplification.

When the detector molecule is a DNA labeled antibody or a DNA oligonucleotide, the nucleic acid moiety may be directly subjected to PCR amplification using conventional conditions. The elevated temperatures which occur during standard PCR amplification reactions are sufficient to release the detector molecule from the ternary complex for amplification.

PCR amplification is performed in the presence of a non-primer detectable probe which specifically binds the PCR amplification product, i.e., the amplified detector DNA moiety. PCR primers are designed according to known criteria and PCR may be conducted in commercially available instruments. The probe is preferably a DNA oligonucleotide specifically designed to bind to the amplified detector molecule. The probe preferably has a 5' reporter dye and a downstream 3' quencher dye covalently bonded to the probe which allow fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable reporter dye is 6-carboxy-tetramethyl-rhodamine (TAMRA). These dyes are commercially available from Perkin-Elmer, Philadelphia, Pa. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. See Heid et al, 1996. This detection system is now commercially available as the TaqMan® PCR system from Perkin-Elmer, which allows real time PCR detection.

In an alternative embodiment, the reporter dye and quencher dye may be located on two separate probes which hybridize to the amplified PCR detector molecule in adjacent locations sufficiently close to allow the quencher dye to quench the fluorescence signal of the reporter dye (de Silva et al., 1998; Rasmussen et al, 1998). As with the detection system described above, the 5'-3' nuclease activity of the polymerase cleaves the one dye from the probe containing it, separating the reporter dye from the quencher dye located on the adjacent probe preventing quenching of the reporter dye. As in the embodiment described above, detection of the PCR product is by measurement of the increase in fluorescence of the reporter dye.

The detector nucleic acid moiety may also be an RNA oligonucleotide. When the detector molecule is an RNA oligonucleotide, the RNA is first reverse transcribed to DNA before PCR amplification (Gibson et al., 1996). It is possible to reverse transcribe an RNA detector molecule directly from the ternary complex. Preferably, the reverse transcription reaction is conducted at an elevated temperature, that is, a temperature sufficient to dissociate the RNA oligonucleotide detector molecule from the ternary complex. Reverse transcription is preferably conducted with avian myeloblastosis virus (AMV) reverse transcriptase since this transcriptase enzyme has been found to work sufficiently well at elevated temperatures required for dissociation of the RNA oligonucleotide from the ternary complex. Preferred temperatures at which the reverse transcription reaction is conducted are about 60° C. to about 70° C. AMV reverse transcriptase is commercially available, for example, from Promega, Madison, Wis. After reverse transcription to DNA, PCR amplification and detection may be performed as described above when the nucleic acid moiety is DNA.

In a preferred embodiment, reverse transcription and PCR amplification are conducted together in a single reaction (RT-PCR). In a particularly preferred embodiment, real time PCR or real time RT-PCR described above are used to detect the PCR product.

In other embodiments of this invention, other real time PCR detection strategies may be used; including known techniques such as intercalating dyes (ethidium bromide) and other double stranded DNA binding dyes used for detection (e.g. SYBR green, a highly sensitive fluorescent stain, FMC Bioproducts), dual fluorescent probes (Wittwer, C. et al., (1977) BioTechniques 22: 130–138; Wittwer, C. et al., (1997) BioTechniques 22: 176–181) and panhandle fluorescent probes (i.e. molecular beacons; Tyagi S., and Kramer FR. (1996) Nature Biotechnology 14: 303–308). Although intercalating dyes and double stranded DNA binding dyes permit quantitation of PCR product accumulation in real time applications, they suffer from the previously mentioned lack of specificity, detecting primer dimer and any non-specific amplification product. Careful sample preparation and handling, as well as careful primer design, using known techniques should be practiced to minimize the presence of matrix and contaminant DNA and to prevent primer dimer formation. Appropriate PCR instrument analysis software and melting temperature analysis permit a means to extract specificity (Ririe, K., et al. (1977) Anal. Biochem. 245: 154–160) and may be used with these embodiments.

The PCR method of the invention has a dynamic range which allows the detection of target molecules at concentrations from about 0.005 pg/mL to about 5000 pg/mL. The method is preferably used to detect target molecules at concentrations in the range of about 1 pg/mL to about 1000 pg/mL.

Utility

The assay of the present invention is useful for the detection of target compounds in clinical diagnosis of physiologic conditions in the same manner as ELISA, immuno —PCR and ELONA have been used conventionally. The assay may also be used to detect the presence of a target compound in food, environmental, water, effluent, etc. samples.

The compounds used in the method of the invention can also be provided in the form of a kit. An assay kit will usually contain the capture molecule, optionally bonded to a solid support and the detector molecule, and may contain one or more of the following: primers for PCR amplification of the nucleic acid moiety, a non-primer probe for quantification during PCR, a calibration standard for a desired target (calibration sample), controls samples containing known amounts/concentrations of the desired target, other PCR reagents used in the PCR steps (alternatively, these reagents can be purchased separately), PCR plates or tubes, optionally coated with a binding molecule, e.g. streptavidin or avidin and instructions for using the reagents and components of the kit to quantify or simply to detect the target in a sample.

Using the method of the invention, detector molecules containing a nucleic acid moiety can be directly detected and quantitated across at least five logarithmic concentrations, to as low as a few hundred molecules. Since amplification and detection occurs directly in PCR tubes in preferred embodiments, there is no need for post-PCR analysis and manipulations and the risk of cross contamination between assays associated with these methods is minimized.

Without further description, it is believed that one of ordinary skill in the art can, using the preceding description and illustrative examples, make and utilize the present invention to the fullest extent. The following working examples therefore specifically point out preferred embodiments of the present invention, and are not to be construed as limiting in any way of the remainder of the disclosure.

EXAMPLES

Example 1

Aptamer Detector Molecule

Aptamer Selection Procedure

VEGF protein was prepared according to known procedures. VEGF aptamer binding buffers was prepared as follow: 1×PBS/1 mM MgCl2.

Thirteen millimeter pop-top membrane holders (Corning Costar Corporation) were wetted with ~50 µl of 1× binding buffer. HAWP 0.45 µM filter, HA filter type (Millipore, Bedford, Mass.), was added to the wetted surface and the top portion of the membrane holder was assembled. RNA was added to binding buffer (at various concentration, depending on the round of selection) at a total volume of 90 µl. The RNA was heat equilibrated at 70° C. for 3 minutes (to denature the RNA) and the RNA was folded by snap cooling the solution on ice. Pre-selection occurred by adding the 90 µl of folded RNA to the filter in the assembled holder. Using a 5 mL syringe, pressure was created to slowly force the solution through the filter and into a capture eppendorf tube.

A 10× concentration of a protein solution (with or without carrier tRNA) in 1× binding buffer was prepared at various concentration, depending on the round of selection. Ten microliters of the 10× protein was added to ~90 µl of pre-selected RNA pool, and then allowed to incubate for 15 minutes at room temperature.

A new filter in a filter holder was wetted and assembled as described above. The protein/RNA solution was passed over the filter (as above), capturing the protein (and RNA bound to the protein). The filter was washed 2 times by passing 200 µl of 1× buffer over the filter. The filter was removed (containing protein/RNA complexes) and placed into an eppendorf tube (flow through RNA was disposed). Four hundred microliters of RNA denaturation solution (20 mM Tris-HCL [pH 8.2], 4M Guanidine-isothiocyanate, 1% β-mercaptoethanol) was then added and the tube was incubated at 70° C. for 15 minute for RNA and protein denaturation. The solution was then removed and placed in a new tube and subjected to precipitation and cleaning as described above. The purified-selected RNA pellet was then redissolved in 20 µl of dH$_2$O.

Reverse transcription-PCR was performed on the captured RNA to make DNA templates for the next round of selection. The rt-PCR reactions included a no reverse transcriptase control, and a no RNA template control. The reactions were performed in 100 µl, containing the following; 1× PCR buffer II (all PCR reagents from Perkin-Elmer, Norwalk, Conn.), 0.2 mM dA/C/G/TTP, 400 nM of primer set #5 (containing T7 promoter sequence, see above), 1.5 mM MgSO$_4$, with ('rt+') or with-out ('rt−') 12.5 Units of MuLV reverse transcriptase (Perkin-Elmer), 2.5 Units of TaqGold DNA polymerase (Perkin-Elmer), with or without 7 µl of purified-selected RNA (see above), and the reactions were brought up to 100 µl with dH$_2$O. Cycling condition for rt-PCR are as follows; 42° C. for 15 minutes, 94° C. for 10 minutes then 12 cycles of 94° C. for 45 seconds, 45° C. for 45 seconds and 68° C. for 1 minute. Agarose gels were prepare (as above, 4% MetaPhor) and 5 µl of the PCR reaction was electrophoresed at 100V for 15 minutes. The gels were visualized and if the 'rt+'band was present over 'rt−' band (at the correct size of 99 base pairs by the DNA standard ladder), and the no template control was not present, the PCR reaction was deemed complete. If no bands are present, the PCR reaction was continued with 2–4 additional PCR cycle steps (same cycle as above) until the appropriate bands are present on the gel.

Once the PCR reaction was complete, the DNA was precipitated and recovered in water and RNA was in-vitro T7 transcribed. The RNA was then acrylamide gel purified, precipitated, cleaned and recovered in water so the concentration could be determined (all steps described above). This RNA was carried through a new round of selection from the top. Repeated cycles of selection at various stringency's were performed by repeating this procedure and varying RNA, protein and tRNA concentrations (see Table 1).

TABLE 1

| Selection Round | [VEGF], nM | [RNA], nM | [tRNA], nM | [Protein]/[RNA] |
|---|---|---|---|---|
| Round #1 | 3000 | 300 | 0 | 10 |
| Round #2 | 3000 | 300 | 0 | 10 |
| Round #3 | 300 | 30 | 1 | 10 |
| Round #4 | 30 | 15 | 1 | 2 |
| Round #5 | 30 | 15 | 5 | 2 |
| Round #6 | 1 | 5 | 5 | 0.2 |

Table 1 shows a selection scheme for obtaining aptamer ligands to VEGF. Round #1 RNA was a random pool RNA sample prepared as previously described (REF?) Each successive round uses the matured RNA pool from the previous round. The introduction of tRNA at round #3 is used to control the selection of non-specific ligands that can bind to selection apparatus (i.e., to the filters or filter holders).

Apatmer Pool Binding Studies

Pool binding was monitored every two rounds. In-vitro RNA transcription was performed using a radiolabeled ribonucleotide (as described above). Purified RNA was diluted to 100 nM and VEGF to 4 µM in 1× binding buffer, both 10-fold concentrations. The RNA solution was heat equilibrate, and five microliters of 100 nM RNA plus either 5 µl of 4 µM VEGF or 5 µl of 1× binding buffer were added to 40 µl 1× binding buffer (10 nM RNA and 400 nM VEGF final reaction concentrations). Samples were incubated at room temperature for 15 minutes. Both 50 µl samples were then separately subjected to filter separation. The filters were then washed and removed (as described above). Total input counts were determined by spotting 5 µl of the 100 nM RNA onto a dry filter. All three filters were allowed to dry. The filters were then exposed to a Phosphorimager screen (Molecular Dynamics, Sunnyvale, Calif.) for 1–12 hours. The screens were read on the Phosphorimager and filter intensities were determined by ImageQuant software (Molecular Dynamics).

Aptamer Pool Cloning

DNA product from the last round of selection was precipitated, cleaned and quantitated (as described above). The DNA pool was then cloned using the PCR-Script™ Amp Cloning Kit (Stratagene, La Jolla, Calif.). Blunt PCR fragments were created by polishing the ends of the PCR fragment in the following mixture; ~5 µg of aptamer PCR pool, 1× polishing buffer, 0.5 units of Pfu DNA polymerase, ~750 nM dNTP mix, brought up in water to a total volume of 13.3 µl. The reaction was incubated on the Perkin Elmer 9600 thermal cycler for 30 minutes at 72° C. A ligation reaction with the pPCR-Script AMP SK(+) cloning vector was carried out in the follows mixture; 1× ligation buffer, 10 ng of pPCR-Script vector, 0.5 mM rATP, 35 ng of polished aptamer PCR pool, 5 units of SrfI restriction enzyme, 4 units of T4-DNA ligase, brought up in water to a total volume of 10 µl. The reaction was allowed to incubate at room temperature for 1 hour. Forty microliters of Epicurian Coli XL1-Blue MRF' Kan supercompetent cells and 0.7 µl of 1.44 M β-mercaptoethanol were mixed and incubated in a tube on ice for 10 minutes. Two microliters of the ligation reaction was added to the cells and the incubation on ice was continued for 30 minutes. This transformation reaction was then heat-pulsed at 42° C. for 45 seconds, and then cooled on ice for 2 minutes. The volume was brought up to 500 µl with SOC medium (20 mM glucose, 2% tryptone w/v, 0.5% yeast extract w/v, 8.5 mM NaCl, 10 mM MgCl$_2$, 10 mM MgSO$_4$) and incubated at 37° C. for 1 hour with 250 rpm shaking. Agar plates containing LB agar, 50 µg/mL carbenicillin, 0.1 mM IPTG and 100 µ/mL X-Gal were prepared and 200, 100 and 50 µl of the transformation reaction was spread onto the agar plates. These plates were incubate at 37° C. overnight. White colonies were picked with sterile pipette tips and replicate plates were made. The pipette tip was then rinsed into a 100 µl PCR cocktail (containing primer set #4, sequencing primers) and PCR was performed for 25 cycles. Five microliters of the PCR reactions were analyzed on 1% agarose gels for the correct insert size, and the remaining 95 µl was purified with a Microcon-30 size exclusion column (Amicon, Beverly, Mass.). Sequencing reactions were prepared to include the following; 8 µl of Big Dye terminator ready reaction mixture (Perkin Elmer), 1 µl of purified M13-aptamer fragment, 3.2 pmol of primer #4a, and water to a total volume of 20 µl. The sequencing reaction was cycled (96° C. for 10 seconds, 50° C. for 5 seconds and 60° C. for 4 minutes) on a Perkin Elmer 9600 thermal cycler 25 times. The reaction was then size exclusion spin column purified using a Centri-Sep™ column (Princeton Separations, Adelphia, N.J.). The sequencing sample was dried in a speed vacuum and brought up in 12 µl of Template Suppression Reagent (Perkin Elmer). Six microliters of this sample was analyzed on an ABI-310 capillary electrophoresis instrument (Perkin Elmer) under sequencing mode. Sequence information was interpreted by the Sequence Analysis software provided with the instrument. Sequence analysis and alignments were performed using the program Sequencher (Gene Codes, Ann Arbor, Mich.) and GeneWorks (IntelliGenetics Inc., Mountain View, Calif.).

Aptamers obtained by this process are shown in the Tables below.

TABLE 2a

Consensus Family A

Clone V03 (SEQ ID NO: 1)

GGGAAUGGAUCCACAUCUACGAAUUCUUUGAAGAGGGUCAAUC<u>CGCGCAC</u>
<u>GU</u>UACGUUCACUGCAGACUUGACGAAGCUU

Clone V04 (SEQ ID NO: 2)

GGGAAUGGAUCCACAUCUACGAAUUCGGGAACAGCUCUAUUC<u>CGCGCACG</u>
<u>U</u>UUGAGUUCACUGCAGACUUGACGAAGCUU

Clone V05 (SEQ ID NO: 3)

GGGAAUGGAUCCACAUCUACGAAUUC<u>CGCGCACGU</u>AGGUUGGGUGUAACU
GCGUUGUUCACUGCAGACUUGACGAAGCUU

Clone V06 (SEQ ID NO: 4)

GGGAAUGGAUCCACAUCUACGAAUUC<u>CGCGCACGU</u>AGGUUGGGUGUAACU
GCGUUGUUCACUGCAGACUUGACGAAGCUU

Clone V08 (SEQ ID NO: 5)

GGGAAUGGAUCCACAUCUACGAAUUCAGGUGGAAAGCAAGUUC<u>CGCGCAC</u>
<u>GU</u>UAAUUUCACUGCAGACUUGACGAAGCUU

Clone V10 (SEQ ID NO: 6)

GGGAAUGGAUCCACAUCUACGAAUUC<u>CGCGCACGU</u>CACGGGCCGACACGA
AUAUGGUUCACUGCAGACUUGACGAAGCUU

Clone V13 (SEQ ID NO: 7)

GGGAAUGGAUCCACAUCUACGAAUUC<u>CGCGCGCG</u>CUAACCUUGNGGNGNA
AGUAUGUUCACUGCAGACUUGACGAAGCUU

Clone V19 (SEQ ID NO: 8)

GGGAAUGGAUCCACAUCUACGAAUUCGGAUAUUCe,uns CGCGCACGU-
CAUUUCA
UCAGCUUUCACUGCAGACUUGACGAAGCUU

TABLE 2b

Consensus Family B

Clone V01 (SEQ ID NO: 9)

GGGAAUGGAUCCACAUCUACGAAUUCAGGCAGCGUAGAGGGUU<u>CACUCUG</u>
<u>CCGAG</u>UUUCACUGCAGACUUGACGAAGCUU

Clone V02 (SEQ ID NO: 10)

GGGAAUGGAUCCACAUCUACGAAUUCGAGGGUCC<u>GUCUGCCGAG</u>UCUUGU
AACACCUUCACUGCAGACUUGACGAAGCUU

Clone V07 (SEQ ID NO: 11)

GGGAAUGGAUCCACAUCUACGAAUUCGAUGGCGUUAGUGGGAAUGAU<u>UCU</u>
<u>GCCGAG</u>UUCACUGCAGACUUGACGAAGCUU

Clone V09 (SEQ ID NO: 12)

TABLE 2b-continued

GGGAAUGGAUCCACAUCUACGAAUUCCGU<u>UCUGCCGAG</u>ACUGCACGUGUG
CUUGAAUUCACUGCAGACUUGACGAAGCUU

Clone V18 (SEQ ID NO: 13)

GGGAAUGGAUCCACAUCUACGAAUUCUGUAAGAUUGGUCUCCAG<u>ACUGCC</u>
<u>GAG</u>CUGUUCACUGCAGACUUGACGAAGCUU

Table 2 shows consensus families of aptamers selected to bind to VEGF. Aptamer family A (Table 2a) has a consensus region (bold) on the consensus sequence. Aptamer family B (Table 2b) has a consensus region (bold) on the consensus sequence.

Binding Analysis of Aptamer Clones

Individual clones were radiolabeled and purified as described above. Binding reactions were performed essentially as described above. RNA-protein complexes were separated using a 0.45 $\mu$M nitrocellulose 96-well filter capture plate (Whatman, Springfield Mill, UK). Samples and washes were passed through the well membrane using a 1000 rpm spin (110×g) for 2 minutes in the 96-well capture plate. Total counts were spotted onto dry wells and 200 $\mu$l of Microscint-40 scintillation cocktail (Packard, Meriden, Conn.) was then added and counts were determined in a TopCount scintillation counter (Packard). Percent binding was determined using the total counts as the 100% binding reference.

Twenty one clones from the selection pool were radiolabeled and half log dilutions of VEGF were added to the fixed concentration of the $P^{32}$-RNA. The point at which 50% of the aptamer bound to VEGF (EC50's) was calculated from a four-parameter fit curve applied in the data analysis program Kalidagraph (Synergy Software, Reading, Pa.). The EC50 values were used as a basis to compare the individual aptamers relative binding affinities to VEGF. In this assay format, the EC50's for the 21 cloned VEGF aptamers ranged from 4.52 nM to 73.4nM with a mean EC50 of 20.7 nM. The EC50's for the published aptamers VEGF40 and VEGF126 were 4.15 nM and 19.9nM respectively. The highest affinity aptamers from the selection procedure (V4, V13, V18 and V19 at 4.52 nM, 8.32 nM, 8.52 nM and 7.61 nM respectively) were comparable in range with the published aptamers to VEGF. See Table 3 shown below.

TABLE 3

| VEGF Apatmer Clone | EC50 |
|---|---|
| 1 | 19.0 |
| 2 | 21.3 |
| 3 | 32.6 |
| 4 | 4.52 |
| 5 | 15.3 |
| 6 | 36.9 |
| 7 | 17.3 |
| 8 | 14.4 |
| 9 | 24.2 |
| 10 | 31.4 |
| 11 | 28.2 |
| 12 | 11.6 |
| 13 | 8.32 |
| 14 | 13.1 |
| 15 | 22.2 |

TABLE 3-continued

| | EC50 |
|---|---|
| 16 | 9.83 |
| 17 | 73.4 |
| 18 | 8.52 |
| 19 | 7.61 |
| 20 | 22.3 |
| 21 | 13.4 |
| Mean | 20.7 |
| Median | 17.3 |
| Pulished Aptamers | |
| 40 | 4.15 |
| 126 | 19.9 |

Table 3 shows calculated EC50 values from the binding curves of $P^{32}$-labeled aptamer binding to VEGF. These values were used as a basis to determine the highest binding affinity aptamers to VEGF (shaded).

Detecting Vascular Endothelial Growth Factor (VEGF) Using the Aptamer rt-PCR Assay of the Invention This assay was adapted from a reported assay (Rodriguez et al., 1998). Coating of anti-VEGF monoclonal antibody (clone 3.5F8) was performed at 0.4 µg/mL in a 0.05 M carbonate buffer (pH=9.6) using various 96-well supports, including; Nunc-immuno MaxiSorp plates (Nalge Nunc International, Naperville, Ill.), Costar polycarbonate PCR plates (Corning Costar Corporation, Cambridge, Mass.) and Perkin-Elmer MicroAmp reaction tubes (Perkin-Elmer, Norwalk, Conn.). The wells were coated with 50 µl of the coating solution and the antibody was passively absorbed to the supports at 2–8° C. for 12–24 hours.

Plates were washed with a 1×PBS (136.9 mM NaCl, 2.68 mM KCl, 7.96 mM $Na_2HPO_4$, 1.47 mM $KH_2PO_4$, pH=7.2)/0.05% Polysorbate 20 wash solution. The plates were washed with either a gravity feed 96-well plate washing system or by the addition of 200 µl of wash solution and then the contents were dumped, repeating the wash 3 to 5 times. Immuno-assay plates were blotted gently on a dry paper towel to remove any residual wash solution. Washing and drying was performed between each immuno-assay step.

Immuno-assay wells were blocked with 100 µl of Assay Buffer (1× PBS, 0.5% BSA, 350 mM NaCl, 5 mM EDTA, 0.05% Tween 20, 0.01% Proclin-300) for 1–2 hours at room temperature with agitation.

Protein samples were diluted in Assay Buffer. Fifty microliters of sample was added to the immuno-assay wells and allowed to incubate at room temperature with agitation for 1 hour.

When colormetric detection was performed, 50 µl biotinylated anti-VEGF monoclonal antibody (clone A4.6.1, 100 ng/mL in Assay Buffer) was added per well and allowed to incubate for 1 hour at room temperature with agitation. Zymed streptavidin HRP was then diluted 1/10000 in Assay Buffer and 50 µl was added to washed wells and allowed to incubate for 30 minutes at room temperature with agitation. Substrate incubations were performed by adding 100 µl of a solution with 5 µg of o-phenylenediamine dihydrochloride and 12.5 mL 1×PBS/0.012% $H_2O_2$ to each washed well. The plates were allowed to incubate at room temperature until sufficient color development occurred. The reaction was stopped with 100 µl of 4.5N $H_2SO_4$ and the plates were read on a SLT EAR340AT platereader with a reference wavelength of 405 nm and a detection wavelength at 492 nm.

When rt-PCR was performed, 50 µl of 10 nM aptamer solution in aptamer buffer (1×PBS, 0.5% BSA, 1 mM $MgCl_2$) was add per well and allowed to incubate for 30 minutes at room temperature with agitation. Plates were then washed with 150 µl of aptamer wash buffer (1×PBS, 1 mM $MgCl_2$) ten times, blotting the plate dry on a paper towel between each wash. Fifty microliters of rt-PCR mixture was added per well (see below), and the plates were covered with a Thermowell Sealing Mat (Corning Costar) and added to a thermal cycler (Perkin Elmer 9600) where the reverse transcription incubation was performed. Forty microliters of the reaction mixture was removed and then added to MicroAmp optical 96-well reaction plates (Perkin Elmer). PCR was continued while data collection occurred on the detection thermal cycler (TaqMan®, ABI Prism 7700 Sequence Detector System, Perkin-Elmer).

Sequence Information

VEGF40 and VEGF126 are published aptamer sequences that have reported Kd's of 0.19 nM and 0.14 respectively (Jellinek et al, 1994). Published aptamers were produced by synthesizing a single stranded DNA template containing the aptamer sequence information and primer binding sites, as follows;

VEGF40:
5'-GGGAGCTCAGAATAAACGCTCAAGACCCATCG-TCAACGGTTGAGTCTGTCCCGTTCGACATGAGGC-CCGGATCCGGC-3'(SEQ ID NO: 14),

VEGF126:
5'-GGGAGCTCAGAATAAACGCTCAAACGGTTCTG-TGTGTGGACTAGCCGCGGCCGTTCGACATGAGG-CCCGGATCCGGC-3'(SEQ ID NO: 15).

To make double stranded DNA template, the following primer set was used (underlined portion is a T7 promoter), Primer #1a:
5'-CCGAAGCTTAATACGACTCACTATAGGGAGCTC-AGAATAAACGCTCAA-3'(SEQ ID NO: 16), Primer#1b: 5'-GCCGGATCCGGGCCTCATGTCGAA-3' (SEQ ID NO: 17).

The ds-DNA templates were used in an in-vitro T7 transcription method to produce RNA (see below).

Primer sets #2 (VEGF40) & #3 (VEGF126) plus probes were used for aptamer detection on the ABI Prism 7700. Primers in set #4 are M13-primers for sequencing of cloned aptamer fragments.

Primer #2a: 5'-ATAAACGCTCAAGACCCA-3'(SEQ ID NO: 18),

Primer #2b: 5'-CCGGGCCTCATGTC-3'(SEQ ID NO: 19),

Probe #2: 5'-FAM-CGTCAACGGTTGAGTCTGTCCC-TAMRA-3'(SEQ ID NO: 20),

Primer #3a: 5'-AGAATAAACGCTCAAACG-3'(SEQ ID NO: 21),

Primer #3b: 5'-GCCTCATGTCGAACG-3', (SEQ ID NO: 22)

Probe #3: 5'-FAM-CCGCGGCTAGTCCACACA-TAMRA-3'(SEQ ID NO: 23),

Primer #4a: 5'-CCCAGTCACGACGTTGTAAAACG-3' (SEQ ID NO: 24),

Primer #4b: 5'-AGCGGATAACAATTTCACACAGG-3' (SEQ ID NO: 25),

All primers and probes were selected to minimize primer/probe dimers using Oligo 5.0 software (National Biosciences, Inc., Plymouth, Minn.) or Primer Express software (Perkin Elmer).

The 30 base random library and primer set #5 (underlined portion is a T7 promoter) was obtained from Dr. Andrew Ellington (Department of Chemistry, Indiana University), Library: 5'-GGGAATGGATCCACATCTACGA[-30N-]TTCACTGCAGACTTG ACGAAGCTT-3'(SEQ ID NO: 26), Primer #5a:
5'-GATAATACGACTCACTATAGGGAATGGATCCAC-ATCTACG A-3'(SEQ ID NO: 27),
Primer #5b: 5'-AAGCTTCGTCAAGTCTGCAGTGAA-3' (SEQ ID NO: 28).

PCR/rt-PCR Reactions, Agarose Gel Electrophoresis and Imaging

PCR/rt-PCR reactions were performed with EZ rTth RNA PCR kit (Perkin Elmer) unless specified otherwise. PCR reaction components included; 1× rTth Buffer or 1× Taq-Man® rTth Buffer (with reference dye), 3 mM Mn(OAc)$_2$, 300 μM dG,A,T&CTP, 10 Units of rTth DNA Polymerase, 200 μM probe (for TaqMan® detection) and 100 μM of each primer. Thermal cycling was performed either in a Perkin Elmer 9600 or ABI Prism 7700 Sequence Detector (Perkin Elmer). A typical cycle included 70° C. for 1 minute (aptamer unfolding), 60° C. for 15 minutes (reverse transcription), 94° C. for 2 minutes then 50 cycles at 94° C. for 15 seconds and 58° C. for 1 minute (the first two incubations were omitted for PCR analysis).

DNA samples were analyzed on 4% submarine agarose gels using MetaPhor agarose (FMC, Rockland, Me.). The solid agarose was added to filtered 1× TBE (89 mM Tris-base, 89 mM Boric acid, 2.5 mM EDTA, pH ~8.2) and heated until dissolved. Ethidium bromide was add to the hot agarose at a final concentration of 0.5 μg/mL. Gels were poured and allowed to cool at room temperature. Samples and standards were loaded in a 0.02% bromophenol blue/7% Glycerol/1× TBE buffer and gels were run in 1× TBE at 120 Volts until sufficient migration occurred. Imaging took place on a FluorImager 545 scanner (Molecular Dynamics, Sunnyvale, Calif.) or a FotoDyne CCD camera imaging system (FotoDyne, Hartland, Wis.). The FluorImager has a flat bed scanner performing a 480 nm laser excitation with specific band pass filters used for emission detection (610 nm for ethidium bromide). The PhotoDyne system used UV excitation of ethidium bromide to image the gels.

DNA or RNA Purification by TBE-Acrylamide Gel Electrophoresis and Nucleic Acid Precipitation DNA/RNA was purified by running samples on 10% polyacrylamide gels (Novex, San Diego, Calif.) with 1× TBE in the gel and buffer. Samples were run at 180 volts for 1 hour. The DNA/RNA was visualized with a PEI plate under long pass UV light. The DNA/RNA band was excised and the gel piece was placed into a tube containing 400 μl of water. The tube was then incubated at 70° C. for 2 hours or 37° C. overnight (with mixing) to elute the DNA/RNA. The 400 μl of water/DNA/RNA was removed and placed in a clean tube for precipitation. DNA/RNA was precipitated by adding 0.1 volumes of 3M Sodium Acetate, 1 μl of 20 mg/mL glycogen and 2 volumes of 100% ethanol. Samples were placed on dry ice for 30 minutes and then spun at maximum speed (~12,000×g) for 30 minutes. Two 70% ethanol washes were performed (400 μl of 70% ethanol wash) and the sample was re-pelted with a maximum speed spin (~12,000×g) for 5 minutes. The supernatant was removed and the pellet was allowed to air dry for about 3 minutes. Pellets were then dissolve in 20 μl of water and concentrations were determined by 260 nm absorbance reading of a 1/200 dilution.

In-Vitro T7 RNA Transcription

T7 reactions were carried out using a AmpliScribe kit (Epicentre Technologies, Madison, Wis.). The reaction contents are as follows; 1× reaction buffer, 10 mM DTT, 7.5 mM A,C,G&UTP, 1 μl T7 AmpliScribe Enzyme mix, 1–2 μl of precipitated DNA template (see above) bring the volume to bring the volume to 10 μl. In radioactive RNA labeling, cold CTP was lowered to 0.75 mM and 1 μL of 400 Ci/mmol, 10 mCi/mL [α-P$^{32}$]CTP (Amersham Pharmacia Biotech, Arlingtion Heights, Ill.) was added. Incubations occurred at 37° C. f or 2–12 hours. Template DNA was cleaved by addition of 0.5 μl of DNase I from the kit and incubated at 37° C. for 15 minutes. All RNA was then TBE-acrylamide gel purified, precipitated and the RNA concentration determined as described above.

Comparison of Various Aptamers to VEGF in the Immuno-Aptamer rt-PCR Assay

Figure 3:
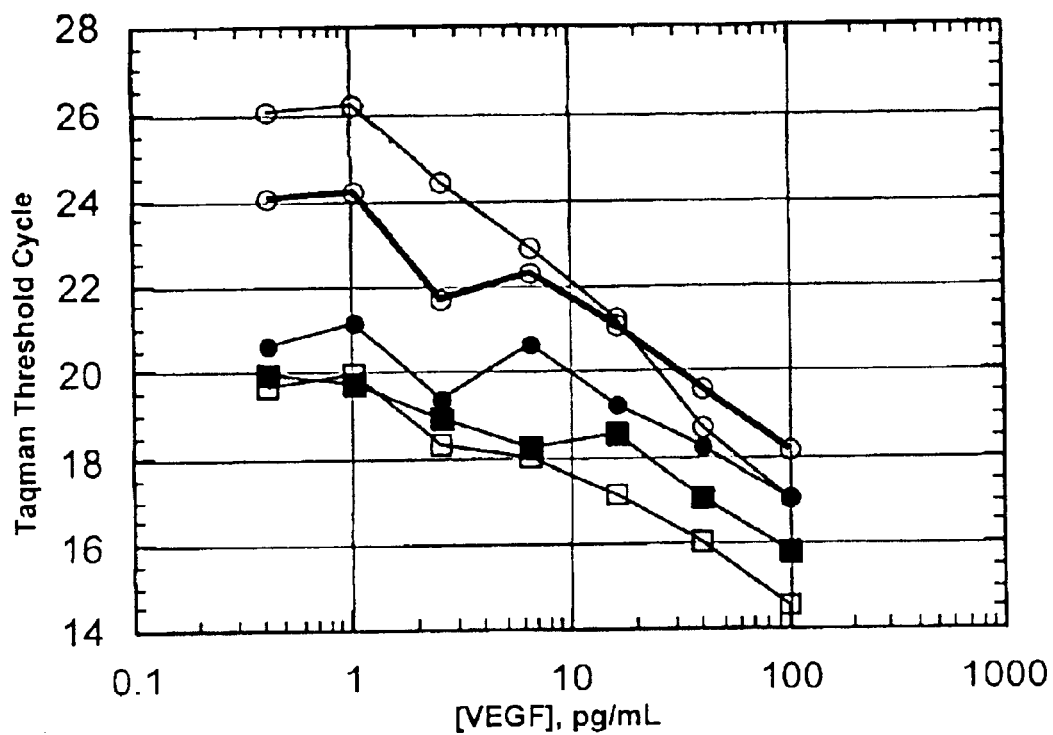
FIG. 3 shows a comparison of published and selected aptamers to VEGF in the immuno-aptamer rt-PCR assay of the invention using TaqMan® detection, including aptamers; VEGF40 (□), VEGF126 (○, thin line), V04 (●), V18 (■) and V19 (○, thick line).

To demonstrate the use of other aptamers as binding reagents in the assay format, the two published aptamers (VEGF40and VEGF126) w ere compared to the selected aptamers V04, V18 and V19. The assay was essentially the same as above, but it used a VEGF analyte range starting at 100 pg/mL and 2.5-fold dilutions down to 0.41 pg/mL. The results demonstrated that all the aptamers could detect down to approximately 1 pg/mL of VEGF analyte. Each aptamer gave a different range of $C_t$'s for the VEGF standard curve. The V18 clone gave only a four $C_t$ difference between the 100 pg/mL and the 1 pg/mL standard, while the VEGF126 aptamer gave the greatest $C_t$ range, a 9 $C_t$ difference between the 100 pg/mL and the 1 pg/mL standard. See FIG. 3.

Specificity of the Immuno-Aptamer rt-PCR Assay

Figure 4:
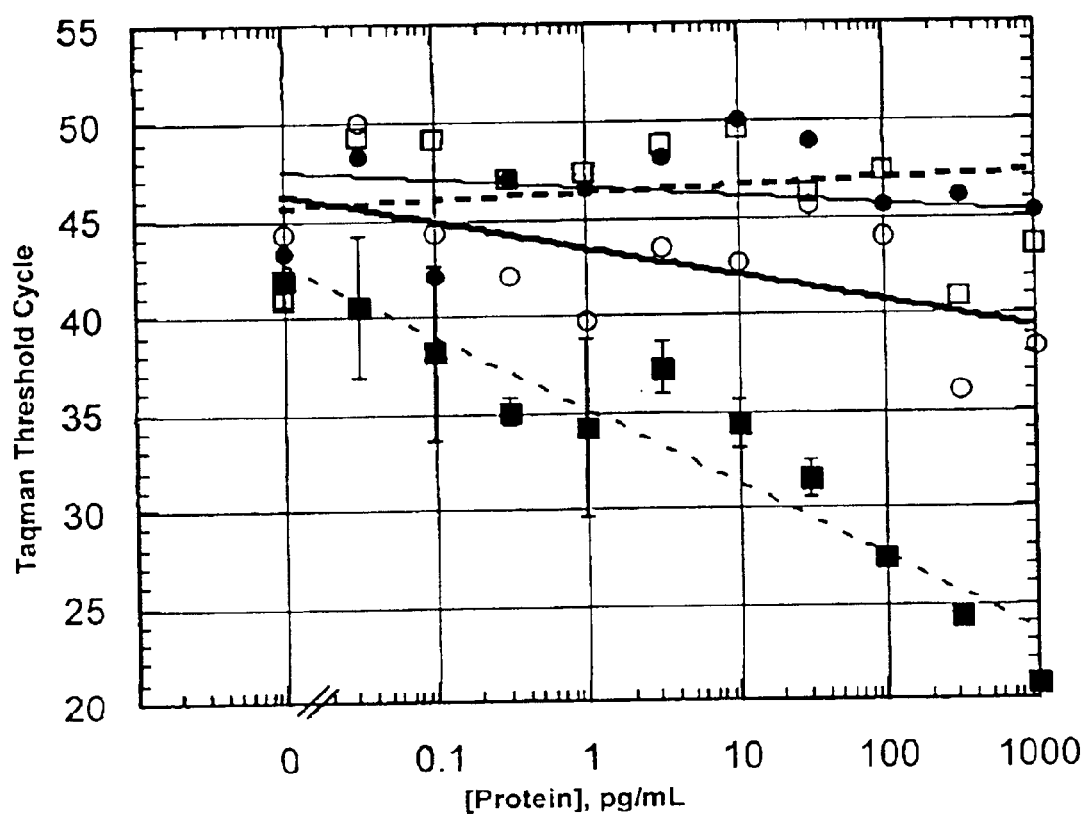
FIG. 4 shows full aptamer PCR with detection on the TaqMan® system using the method of the invention, and a comparison of VEGF standard curve (■) to an immuno-absorbed VEGF standard curve (○), DNase (□) and HGF (●) negative control standard curves.
Figure 5:
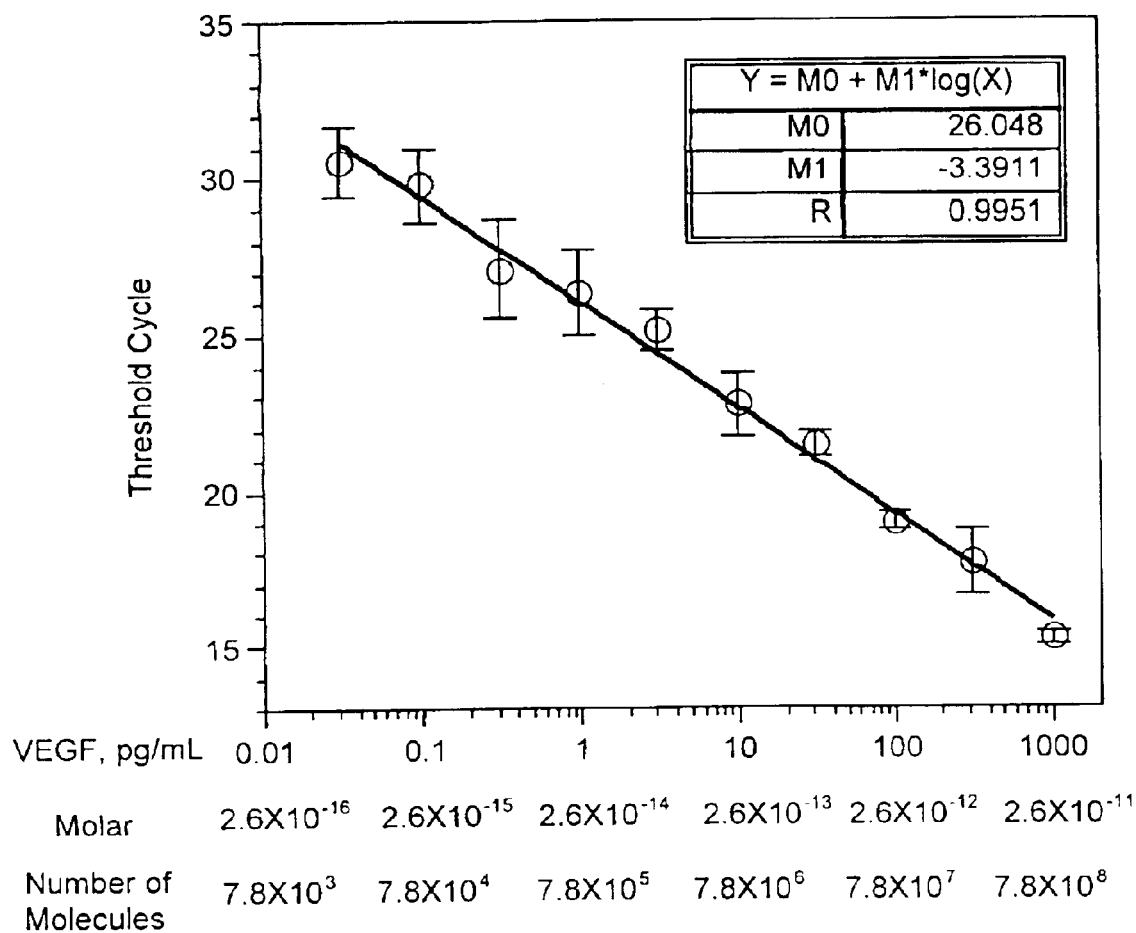
FIG. 5 indicates the sensitivity of the assay of the invention for VEGF. The assay included duplicates for each assay and was repeated three times. The assay used the published aptamer VEGF126 as the detection molecule.

Specifics detection of VEGF analyte was assessed in the immuno-aptamer rt-PCR assay using the TaqMan® detection system. The assay was performed using the TaqMan® to quantitative relative amounts of the detection aptamer. Standard curves of VEGF, HGF and DNase analytes were compared, as well as an immuno-absorbed VEGF standard curve (using excess amounts of coat antibody in solution with the VEGF). VEGF specific signal was linear from 1000 pg/mL to 3.1 pg/mL with good precision. The dilution series from 1 pg/mL to 0.031 pg/mL of VEGF trended in the same direction as higher analyte concentrations, but variation in the replicates was much greater than the 1000–3.1 pg/mL range. See FIG. 4.

Sensitivity of Detection of VEGF in the Immuno-Aptamer rt-PCR Assay

The sensitivity of detecting VEGF in the assay was evaluated by repeating VEGF standard curves that encompassed a large detection range (1000 pg/mL to 0.031 pg/mL of VEGF). The samples were run in duplicate and the assay was repeated three times. This assay also incorporated a vacuum driven hand washer that had a gravity feed wash buffer delivery system. The assay was able to detect a linear dose response signal down to 0.03 pg/mL of VEGF. There was a detectable VEGF specific signal down to 0.31 pg/mL that was distinguishable from 1 standard deviation of the blank.

Detection of VEGF in Serum Samples

Figure 6:
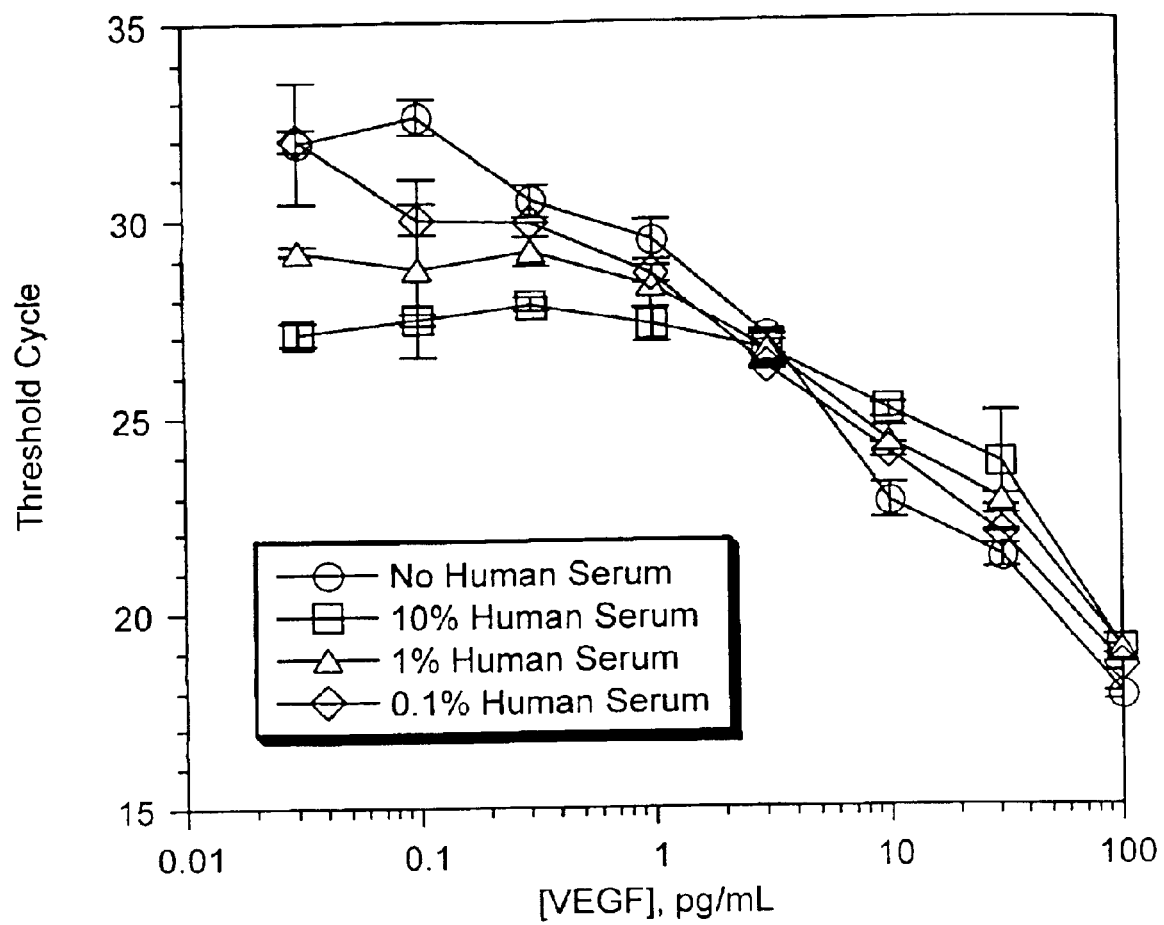
FIG. 6 shows a comparison of VEGF spike detection in a 10% human serum matrix (○) versus normal assay buffer conditions (□). The immuno-aptamer rt-PCR assay used the published aptamer VEGF126 as the detection reagent.

Various VEGF concentration were exogenously added to dilutions of an individual human serum and quantitated in the aptamer rt-PCR assay. The patient sample was determined to have 79.9 pg/mL of VEGF in the neat serum by ELISA. At 10% and 1% human serum concentrations in the aptamer rt-PCR assay, the endogenous levels of VEGF were seen as a plateau of signal. At VEGF concentrations above this plateau level, the quantitation showed good correlation with the no human serum control, suggesting the endogenous nucleases were not effecting the aptamer binding reagent. The normal washing employed in the immunoassay portion of the assay was sufficient to remove sufficient levels of endogenous nuclease so that the quantitation was not effected. The 0.1% human serum VEGF curve was identical to the no human serum control. Endogenous levels of VEGF were diluted to low enough levels to not result in the plateau effect seen at high human serum concentrations. See FIG. 6.

Example 2

DNA Labeled Antibody Detector Molecule

Primers, Probe, and DNA Label

The 71 base DNA label, 5'CCAACCTCCTGTCCAC-CAACTCTTTCGTTGGATGTATCTGCG-GCGTTTATGTTGGTTCTCCTGGACTGGAA3' (SEQ ID NO: 29), was derived from DNA sequence of the woodchuck hepatitis B virus (Genbank locus OHVHEPBA). The DNA label was synthesized by using standard β-cyanoethyl phosphoamidite chemistry on a DNA synthesizer (Applied Biosystems). To introduce a sulfhydryl to the DNA, the 5'-thiol-modifier C6(S-trityl-6-mercaptohexyl)-(2-cyanoethyl)-(N,N-diisopropyl)-phosphoramidite (Glen Research, Sterling, Va.) was attached during synthesis. The upper primer, 5'CCAACCTCCTGTCCACCAAC 3'(SEQ ID NO: 30), the lower primer, 5' TTCCAGTCCAG-GAGAAACCAACA 3'(SEQ ID NO: 31), and the probe, 5' CTTTTCGTTGGATGTATCTGCGGCGTTT 3'(SEQ ID NO: 32), sequences were designed by the computer program Primer Express 1.0 (PE Applied Biosystems).

The primers were purchased from Research Genetics (Huntsville, Ala.) and the probe was purchased from PE Applied Biosystems or Biosearch Technologies (Novato, Calif.). The probe was synthesized with the reporter dye FAM (6-carboxyfluorescein) at the 5' end and the quencher dye TAMRA (6-carboxy-tetramethylrhodamine) at the 3'. The 3' end also has a phosphate group to prevent extension during PCR amplification.

DNA—Antibody Conjugation

A buffer exchange into buffer 1 (0.5 M sodium bicarbonate, 1 mM EDTA, pH 8.5) was carried out for the antibody by either a nap 5 or PD 10 desalting column (Pharmacia Biotech, Piscataway, N.J.). A 25 molar excess of the crosslinker Sulfo-SMCC (sulfosuccinimidyl 4-[N-maleimidomethyl]-cyclohexane-1-carboxylate) (Pierce, Rockford, Ill.), which reacts to the primary amines of the antibody, was added and the mixture was incubated in the dark for 4 h at room temperature.

The trityl group protecting the sulfhydryl on the DNA label was removed. Aqueous silver nitrate was added to the DNA label which was suspended in triethylammonium acetate and the silver was precipitated by adding excess dithiotheritol (DTT) as described by the manufacturer. The supernatant was filtered by a spin-x 45 μm filter (Costar, Cambridge, Mass.) and the precipitate was washed 3 times with PBS (8 mM sodium phosphate, 1.5 mM potassium phosphate, 2.7 mM KCl, 137 mM NaCl, pH 7.2).

A buffer exchange into buffer 2 (0.1 M sodium phosphate, 1 mM EDTA, pH 6.5) was carried out for the antibody-SMCC complex and the DNA label by PD 10 columns. The antibody was concentrated to 1 to 2 ml with a centricon 30 (Amicon, Beverly, Mass.). The DNA was added to the antibody in a 10 fold molar excess and incubated overnight at room temperature.

A 1 ml protein A column was equilibrated with buffer 3 (1.5 M glycine, 300 mM NaCl, pH 8.3). The DNA-antibody mixture was loaded and the column was washed with Buffer 3 until the OD 260 and OD 280 returned to baseline (approximately 5 column volumes). The antibody was eluted with buffer 4 (Buffer 3 with 2.5 M $MgCl_2$) and dialyzed into PBS.

VEGF Immuno-PCR

Figure 7:
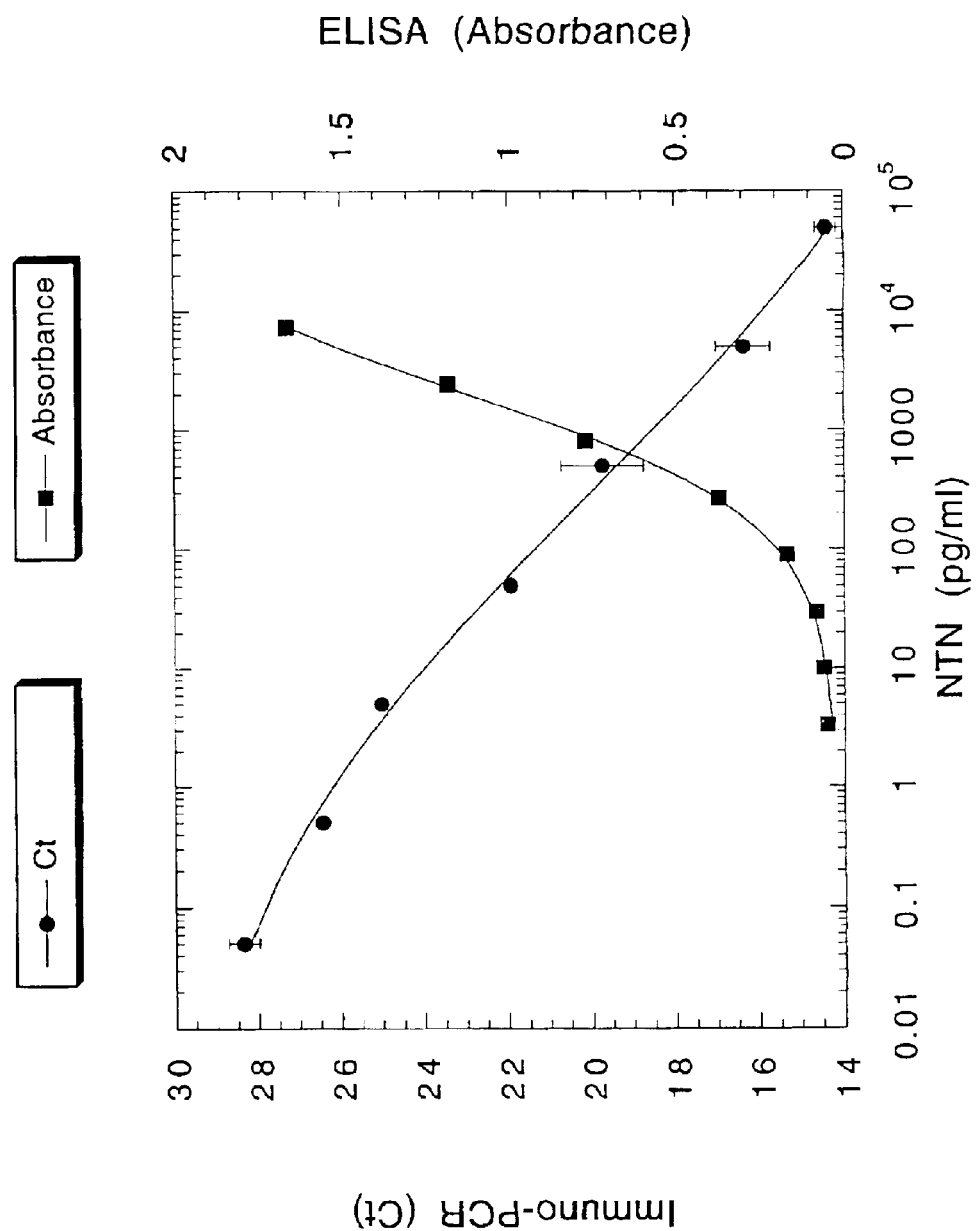
FIG. 7 shows comparative results for a VEGF assay in ELISA format and the immuno-PCR format of the invention (Example 2).

1 μg/ml biotinylated monoclonal capture antibody (3.5F8), the sample, and 1:1.5K dilution of the DNA conjugated monoclonal detecting antibody (A4.6.1) were incubated in polystyrene Microwell plates (Nunc, Roskilde, Denmark) for 2 h at room temperature. The buffer was PBS, 0.5% BSA, 0.05% Tween 20, 0.35 M NaCl, 1 mM EDTA, 0.25 μg/ml calf thymus DNA (Sigma, St. Louis, Mo.), pH 7.2 (Buffer 5). Streptavidin coated PCR tubes (Boehringer Mannheim, Indianapolis, Ind.) were blocked with 200 μl/well of buffer 6 (PBS, 0.5% BSA, 0.05% Tween 20, 0.25 μg/ml calf thymus DNA) for 1 to 2 h at room temperature. 50 μl of the sample mixture was transferred to the PCR tubes and incubated for 30 min. at room temperature. The tubes were washed 10 times with 200 μl/well of PBS and tapped dry on absorbent paper. They were stored at −20° C. if the PCR step was not immediately performed. See FIG. 7.

NTN Immuno-PCR

Figure 8:
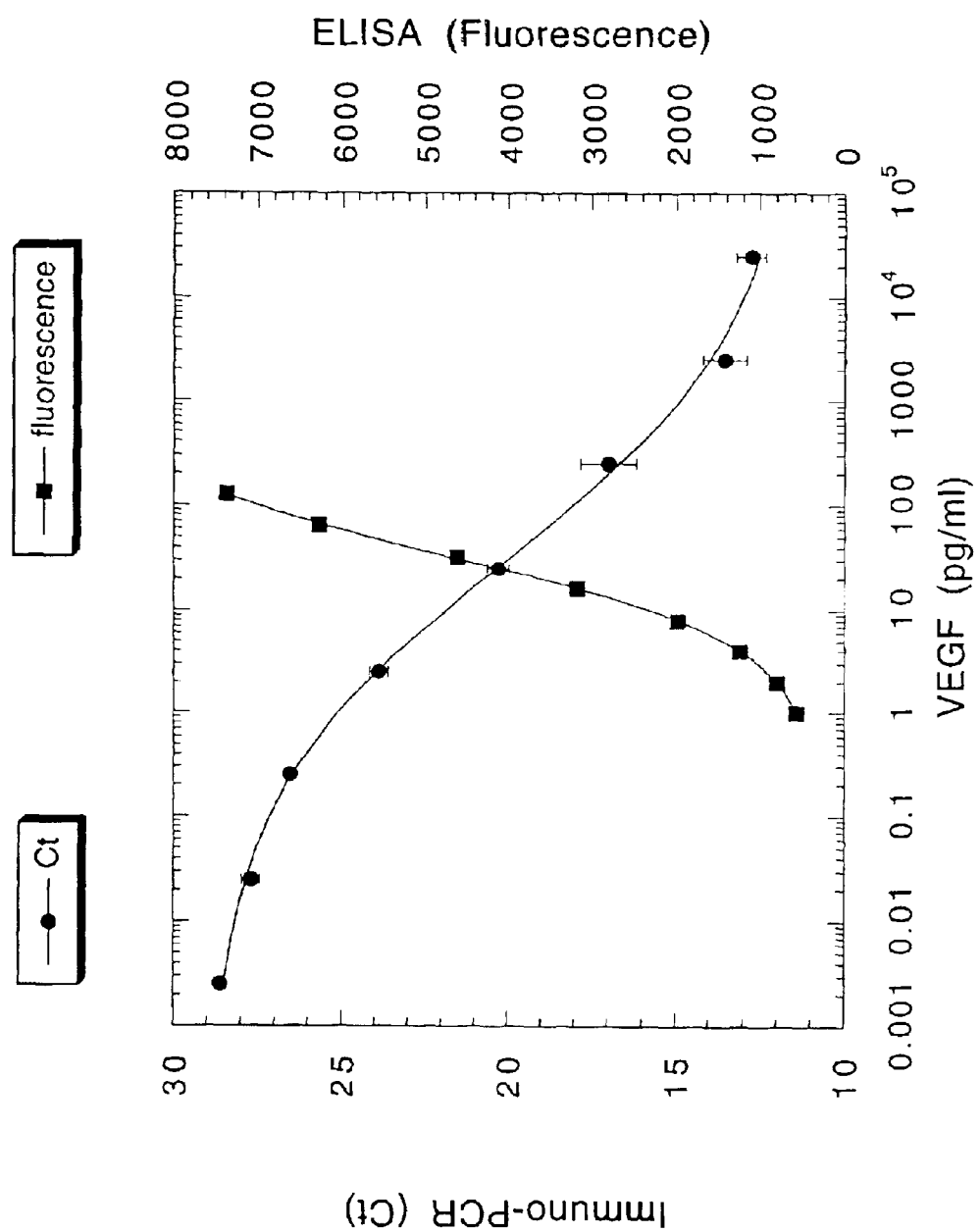
FIG. 8 shows comparative results for a NTN assay in ELISA format and the immuno-PCR format of the invention (Example 2).

The NTN immuno-PCR procedure is similar to that of the VEGF except that buffer 6 was used for the sample incubation step instead of buffer 5. The concentration for the biotinylated monoclonal capture antibody (2208) was 10 μg/ml and the DNA conjugated monoclonal detecting antibody (2209) was used at 1:1.5K. See FIG. 8.

Real-Time PCR

Buffer A, nucleotides, ampli-Taq gold polymerase, AmpErase uracil N-glycosylase (UNG) and $MgCl_2$ were purchased from PE Applied Biosystems. 50 el/well of master mix (2.5 mM $MgCl_2$, 1× Buffer A, 0.5 μM upper primer, 0.5 μM lower primer, 40 nM probe, 200 μM of ATP, GTP, and CTP, 400 μM of UTP, 0.5 unit UNG, 1.5 units Taq polymerase) was added to the PCR tubes containing the antibody-antigen complex and sealed with optical caps (PE Applied Biosystems). The thermocycle conditions for the Taqman® were 50° C. for 3 min, 94° C. for 12 min, and 40 cycles of 94° C. for 15 s and 60° C. for 1.5 min. Data was collected during the extension phase.

The threshold emission was calculated by the Sequence Detector 1.6 software (PE Applied Biosystems) as 10 standard deviations above the average increase in reporter dye emission due to the cleavage of the probe (ΔRn), of cycles 3 to 10. The $C_t$ value for each sample was determined by the software and exported to Softmax Pro (Molecular Devices, Sunnyvale, Calif.) for data reduction. The standard curve was fit using a four parameter non-linear regression.

NTN Colormetric ELISA

Maxisorp plates (Nunc) were coated overnight at 4° C. with 100 μl/well of 1 μg/ml 2208 in buffer 7 (50 mM $Na_2CO_3$, pH 9.6). The plates were blocked with 200 μg/well of buffer 8 (PBS, 0.5% BSA, pH 7.2) for 1 h at room temperature. The standards (7290–10 pg/ml) and samples were diluted into buffer 9 (Buffer 8, 0.05% Tween 20) and incubated on the plate for 2 h. 0.25 μg/ml biotinylated 2209 was incubated on the plate for 1 h followed by 1:100K of Streptavidin-HRP (Amdex, Copenhagen, Denmark) for 30 min. The substrate 3,3'5,5'-tetramethyl benzidine (TMB) (Kirkegaard & Perry, Gaithersburg, Md.) was added. After 5 minutes, the reaction was stopped with 1 M $H_3PO_4$: Between each step, the plates were washed with PBS+0.05% Tween 20. The absorbance was read at 450/620 nm on a Titerek stacker reader (ICN, Costa Mesa, Calif.). The standard curve was fit by the Softmax Pro using a four parameter regression.

All references cited herein are hereby expressly incorporated by reference.

While the invention has necessarily been described in conjunction with preferred embodiments and specific working examples, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by letters patent hereon be limited only by the appended claims and equivalents thereof.

REFERENCES

ABI Prism® 7700 Sequence Detection User's Manual: Section D, Theory of Operation. pgs D-1 to D-22. January 1998.

Allen, P.; Worland, S.; Gold, L. (1995). Isolation of high-affinity RNA ligands to HIV-1 integrase from a random pool. Virology. 209(2): 327–336.

Andrake, M.; Guild, M.; Hsu, T.; Gold, L.; Tuerk, C.; Karam, J. (1988). DNA polymerase of bacteriophage T4 is an autogenous translational repressor. Proc. Nat. Acad. Sci. U.S.A. 85: 7942–46.

Becker-Andre, M (1991) Meth. Mol. Cell. Biol. 2: 189–201.

Binkley, J.; Allen, P.; Brown, D. M.; Green, L.; Turek, C.; Gold, L. (1995). RNA ligands to human nerve growth factor. Nucl. Acid Res. 23(16): 3198–3205.

Bless, N. M.; Smith, D.; Charlton, J.; Caermak, B. J.; Schmal, H.; Friedl, H. P.; Ward, P. A. (1997). Protective effects of an aptamer inhibitor of neutrophil elastase in lung inflammation injury. Curr. Biol. 7(11): 877–880.

Bock, L. C.; Griffin, L. C.; Latham, J. A.; Vermass, E. H.; Toole, J. J. (1992). Selection of single-stranded DNA molecules that bind and inhibit human thrombin. Nature. 355(6360): 564–566.

Boutin et al. (1998). *Proc. Natl. Acad. Sci. USA,* 88: 7744–7748.

Brown, D.; Gold, L. (1995). Template recognition by an RNA-dependent RNA polymerase: identification and characterization of two RNA binding sites on Q beta replicase. Biochemistry. 34(45): 14765–14774.

Brown, L. F.; Betmar, M.; Claffey, K.; Nagy, J. A.; Feng, D.; Dvorak, A. M.; Dvorak, H. F. (1997.) Vascular permeability factor/vascular endothelial growth factor: a multifunctional angiogenic cytokine. Regulation of Angiogenesis. Edit by Goldberg & E. M. Rosen, Basel, Switzerland. pgs 250–252.

Brown, L. F.; Yeo, K. T.; Berse, B.; Yeo, T. K.; Senger D. R.; Dvorak, H. F.; van de Water, L. (1992). Expression of vascular permeability factor (vascular endothelial growth factor) by epidermal keratinocytes during wound healing. J. of Exp. Med. 176(5): 1375–1379.

Bruno, J. G. (1997). In-vitro selection of DNA to chloro-aromatics using magnetic microbead-based affinity separation and fluorescence detection. Bioch. and Biophy. Res. Comm. 234(1): 117–120.

Burke D. H.; Gold L. (1997). RNA aptamers to the adenosine moiety of S-adenosyl methionine: structural inferences from variations on a theme and the reproducibility of SELEX. Nuc. Acids Res. 25(10): 2020–2024.

Burgess, G. W., ed. (1988). *ELISA Technology in Diagnosis and Research.* Graduate School of Tropical Veterinary Science, James Cook University of North Queensland, Townsville, Australia.

Campbell, N. A. (1987). Biology. Chp. 38: 811–812. Circulation and Gas Exchange. The Benjamin/Cummings Publishing Company, Inc., Menlo Park, Calif.

Case, M. et al. (1997) Biochem. Soc. Trans. 25: 374S.

Chang, T. C.; Huang, S. H. (1997). A modified iummnopolymerase chain reaction for the detection of β-glucuronidase from Escherichia coli. J. of Imm. Meth. 208: 35–42.

Charlton, J.; Sennello, J.; Smith, D. (1997). In vivo imaging of inflammation using an aptamer inhibitor of human neutrophil elastase. Chem. & Biol. 4(11): 809–816.

Chen, H.; Gold, L. (1994). Selection of high-affinity RNA ligands to reverse transcriptase: inhibition of cDNA synthesis and Rnase H activity. Biochemistry. 33(29): 8746–8756.

Chen, H.; McBroom, D. G.; Zhu, Y.; North T. W.; Gold, L. G. (1996). Inhibitory RNA ligand to reverse transcriptase from feline immunodeficiency virus. Biochemistry. 35(21): 6923–30.

Connell, G. J.; Yarus, M. (1994). RNAs with dual specificity and dual NAs with similar specificity. Science. 264 (5162): 1137–1141.

Connolly, D. T.; Heuvelman, D. M.; Nelson, R.; Olander, J. V.; Eppley, B. L.; Delfino, J. J.; Siegel, N. R.; Leimgruber, R. M.; Feder, J. (1989). Tumor vascular permeability factor stimulates endothelial cell growth and angiogenesis. J. of Clin. Inv. 84(5): 1470–1478.

Conrad, R.; Keranen, L. M.; Ellington, A. D.; Newton, A. C. (1994). Isozyme-specific inhibition of protein kinase C by RNA aptamers. J. of Biol. Chem. 269(51): 32051–32054.

Conrad, R. C.; Giver, L.; Tian, Y.; Ellington, A. D. (1996). In Vitro Selection of Nucleic Acid Aptamers That Bind Proteins. Meth. in Enzym. 267: 336–367.

D'Andrea et al. (1989). *Cell,* 57: 277–285.

Dang, C.; Jayasena, S. D. (1996). DNA inhibitors of Taq DNA polymerase facilitate detection of low copy number targets by PCR. J. Mol. Biol. 264: 268–278.

Davis, K. A.; Barnaby, A.; Lin, Y.; Jayasena, S. D. (1996). Use of a high affinity DNA ligand in flow cytometry. Nuc. Acids Res. 24(4): 702–706.

Davis et al. (1991). *Science,* 253: 59–63.

Dertmar, M.; Brown, L. E.; Claffey, K. P.; Yeo, K. T.; Kocher, O.; Jackman, R. W.; Berse, B.; Dvorak, H. E. (1994). Overexpression of vacular permeability factor/vascular endothelial growth factor and its receptors in psoriasis. J of Exp. Med. 180(3): 1141–1146.

DeVries, C.; Escobedo, J. A.; Ueno, H.; Houck, K.; Ferrara, N.; Williams, L. T. (1992). The fms-like tyrosine kinase, a receptor for vascular endothelial growth factor. Science. 255: 989–991.

Doudna, J. A.; Cech, T. R.; Sullenger, B. A. (1995). Selection of an RNA molecule that mimes a major autoantigenic epitope of human insulin receptor. Proc. Nat. Acad. Sci. U.S.A. 92(6): 2355–2359.

Drolet, D. W. (1996). *Nature Biotechnology,* 14: 1021–1025.

Drolet, D. W.; Moon-McDermott, L.; Romig, T. S. (1996). An enzyme-linked onligonucleotide assay. Nat Biot. 14: 1021–1025.

Edery et al. (1989). *Proc. Natl. Acad. Sci. USA,* 86: 2112–2116.

Ellingtion, A. D. (1994). RNA selection. Aptamers achieve the desired recognition. Curr. Biol. 4(5): 427–429.

Ellington, A. D. Aptamers: A workshop in in vitro selection. Center for Aptamer Research, The Institute for Molecular and Cellular Biology, Indiana University.

Ellington, A. D. and Szostak, J. W. (1992). Nature (England), 355: 850–852.

Ellington, A. D. and Szostak, J. W. (1990). Nature (England), 346: 818–822.

Ellington, A. D.; Szostak, J. W. (1990). In vitro selection of RNA molecules that bind specific ligands. Nature. 346: 818–822.

Fasco, M. J.; Treanor, C. P.; Spivack, S.; Figge, H. L.; Kaminsky, L. S. (1995). Quantitative RNA-polymerase chain reaction-DNA analysis by capillary electrophoresis and laser-induced fluorescence. Anal. Bioch. 224: 140–147.

Ferrara N.; Henzel, W. J. (1989). Pituitary follicular cells secrete a novel heperin-binding growth factor specific for vascular endothelial cells. Bioch. & Bioph. Res. Comm. 161(2): 851–858.

Ferre, F. (1992) PCR Methods Applic. 2: 1–9.

Fukunaga et al. (1990a). *Cell,* 61: 341–350.

Fukunaga et al. (1990b). *Proc. Natl. Acad. Sci. USA,* 87: 8702–8706.

Gearing et al. (1991). *EMBO J.,* 8: 3667–3676; 10: 2839–2848.

Gibson, U. E. M.; Heid, C. A.; Williams, P. M. (1996). A novel method for real time quantitative rt-PCR. Gen. Meth. 6: 995–1001.

Gibson et al. (I 996). *Genome Methods,* 6: 995–1001.

Giver, L.; Bartel, D. P.; Zapp, M. L.; Green, M. R.; Ellington, A. D. (1993). Selection and design of high-affinity RNA ligands for HIV-1 Rev. Gene. 137: 19–24.

Goodwin et al. (1990). *Cell,* 60: 941–951.

Gorman et al. (1990). *Proc. Natl. Acad. Sci. USA,* 87: 5459–5463.

Greene, R. et al. (1991). Methods (Orlando), 2: 75–86, etc.

Griswold, W. (1987) 8: 145–171.

Harlow, E. R. and Lane, D. W., eds. (1988). *Antibodies—A Laboratory Manual.* Cold Spring Harbor Laboratory, Chapter 6.

Hatakeyama et al. (1989). *Science,* 244: 551–556.

Hayashida et al. (1990). *Proc. Nat. Acad. Sci. USA,* 244: 9655–9659.

Heid, C. A.; Stevens, J.; Livak, K. L.; Williams, P. W. (1996). Real time quantitative PCR. Gen. Meth. 6: 986–994.

Hendrickson, E. R.; Truby, T. M. H.; Joerger, R. D.; Majarian, W. R.; Ebersole, R. C. (1995). High sensitivity multianalyte immunoassay using covalent DNA-labeled antibodies and polymerase chain reaction. Nuc. Acids Res. 23(3): 522–529.

Hendrickson, E. R. (1995). *Nucleic Acids Research,* 23: 522–529.

Hibi et al. (1990). *Cell,* 63: 1149–1157.

Hicke, B. J.; Watson, S. R.; Koenig, A.; Lynott, C. K.; Bargatze, R. F.; Chang, Y.; Ringquist, S.; Moon-McDermott, L.; Jennings, S.; Fitzwater, T.; Han, H.; Varki, N.; Albinana, I.; Willis, M. C.; Varki, A.; Parma, D. (1996). DNA aptamers block L-selectin function in vivo: inhibition of human lymphocyte trafficking in SCID mice. J. of Clin. Invest. 98(12): 2688–2692.

Hnatowich, D. J.; Mardirossian, G.; Rusckowski, M.; Winnard Jr., P. (1996). Protein labelling via deoxyribonucleic acid hybridization. Nuc. Med. Comm. 17: 66–75.

Hoack, K. A.; Leung, D. W.; Rowland, A. M.; Winer, J.; Ferrara, N. (1992). Dual regulation of vascular endothelial growth factor bioavailability by genetic and proteolytic mechanisms. J. of Biol. Chem. 267(36): 26031–26037.

Hollinger et al. (1993). *Proc. Natl. Acad. Sci. USA* 90: 6444–6448.

Ishizaki, J.; Nevins, J. R.; Sullneger, B. A. (1996). Inhibition of cell proliferation by an RNA ligand that selectively blocks E2F function. Nat. Med. 2(12): 1386–1389.

Itoh et al. (1990). *Science,* 247: 324–328.

Jaeger, J. A.; Turner, D. H.; Zuker M. (1989a). Improved Predictions of Secondary Structures for RNA. Proc. Natl. Acad. Sci. U.S.A. 86: 7706–7710.

Jaeger, J. A.; Turner, D. H.; Zuker M. (1989b). Predicting Optimal and Suboptimal Secondary Structure for RNA. Molecular Evolution: Computer Analysis of Protein and Nucleic Acid Sequences. R. F. Doolittle ed. Meth. in Enzym. 183: 281–306.

Jellinek, D.; Green, L. S.; Bell, C.; Janjic, N. (1994). Inhibition of receptor binding by high-affinity RNA ligands to vascular endothelial growth factor. Biochemistry. 33: 10450–10456.

Jellinek, D.; Lynott, C. K.; Rifkin, D. B.; Janjic, N. (1993). High-affinity RNA ligands to basic fibroblast growth factor inhibit receptor binding. Proc. Nat. Acad. Sci. U.S.A. 90(23): 11227–11231.

Jenison, R. D.; Gill, S. C.; Pardi, A.; Polisky, B. (1994). High-resolution molecular discrimination by RNA. Science. 263(5152): 1425–1429.

Joerger, R. D. et al. (1995). *Clinical Chemistry,* 41: 1371–1377.

Jones et al. (1986). *Nature,* 321: 522–525.

Jones et al., (1990). *Blood,* 76: 31–35.

Kawazoe, N.; Ito, Y.; Imanishi, Y. (1997). Bioassay using a labeled oligonucleotide obtained by in vitro selection. Biot. Prog. 13(6): 873–876.

Kohler & Milstein. (1975). *Nature,* 256: 495

Kitamura et al. (1991a). *Cell,* 66: 1165–1174.

Kitamura et al. (1991b). *Proc. Natl. Acad. Sci. USA,* 88: 5082–5086.

Klagsbrun, M.; D'Amore, P. A. (1991). Regulators of angiogenesis. Ann. Rev. of Physiol. 53: 217–239.

Klagsbrun, M.; D'Amore, P. A. (1996). Vascular endothelial growth factor and its receptors. Cytok. & Grow. Fact. Rev. 7(3): 259–270.

Kubik, M. F.; Stephens, A. W.; Schneider, D.; Marlar, R. A.; Tasset, D. (1994). High-affinity RNA ligands to human alpha-thrombin. Nucl. Acids Res. 22(13): 2619–2626.

Keyt, B. A.; Berleau, L. T.; Nguyen, H. V.; Chen H.; Heinsohn, H.; Vandlen, R.; Ferrara, N. (1996). The carboxyl-terminal domain (111–165) of vascular endothelial growth factor is critical for its migtogenic potency. J. of Biol. Chem. 271(13): 7788–7795.

Larsen et al. (1990). *J. Exp. Med.,* 172: 1559–1570.

Kellogg, D. (1990) Anal. Biochem. 189: 202–208.

Lentz, S. J.; Varricchio, M.; Smith, S. G.; Ficsor, G. (1997). Detection of low copy number inversions in mouse genomic DNA with unidirectional PCR primers. Envir. & Mol. Mut. 30(3): 260–263.

Leroith, D.; Bondy, C. (1996). Growth factors and cytokines in health and disease. The vascular endothelial cell growth factor family and its receptors: molecular and biological proterties. JAI press Inc., Greenwich, Conn., pgs 435–436.

Leung et al. (1987). *Nature,* 330: 537–543.

Lin, Y., Sayasena, S. D. (1997). Inhibition of multiple thermostable DNA polymerases by a heterodimeric aptamer. J. Mol. Biol. 271 (1): 100–111.

Lin, Y.; Nieuwlandt, D.; Magallanez, A.; Feistner, B.; Jayasena, S. D. (1996). High-affinity and specific recognition of human thyroid stimulating hormone (hTSH) by in vitro selected 2'-amino-modified RNA. Nuc. Acids Res. 24(17): 3407–3414.

Lorsch, J. R.; Szostak, J. W. (1994). In vitro selection of RNA aptamers specific for cyanocobalamin. Biochemistry. 33: 973–982.

McElhinny, A. (1997) BioTechniques 23: 660–662.

Miemeyer, C. M.; Adler, M.; Blohm, D. (1995). Fluorometric polymerase chain reaction (PCR) enzyme-linked immunosorbent assay for quantification of immuno-PCR products in microplates. Anal. Bioch. 246: 140–145.

Mill, J. W. (1997). Vascular endothelial growth factor and ocular neovascularization. Amer. J. of Path. 151(1): 13–23.

Milstein Kohler & Milstein. (1975). *Nature,* 256: 495.

Morrison et al. (1984). *Proc. Natl. Acad. Sci. USA,* 81: 6851–6855.

Moses, M. A.; Klagsbrun, M.; Shing, Y. (1995). The role of growth factors in vascular cell development and differentiation. Int. Rev. of Cyt. 161: 1–48.

Mosley et al. (1989). *Cell,* 59: 335–348.

Mullis, K. B.; Faloona, F. A. (1987). Specific synthesis of DNA in vitro via a polymerase-catalyzed chain reaction. Meth. in Enz. 155: 225–250.

Mweene, A. (1996) J. Clin. Microbiol. 334: 748–750.

Myoken, Y.; Kayada, Y.; Okamoto, T.; Kan, M.,; Sato, G. H.; Sato, J. D. (1991). Vascular endothelial cell growth factor (VEGF) produced by A-431 human epidermoid carcinoma cells and identification of VEGF memebrane binding sites. Proc. Nat. Acad. Sci. U.S.A. 88(13): 5819–5823.

Nicola et al. (1991). *Cell.* 67: 14.

Niemeyer, C. et al. (1997) Anal. Biochem 246: 140–145.

Numata, Y.; Matsumoto, Y. (1997). Rapid detection of ∝ human atrial natriuretic peptide in plasma by a sensitive immuno-PCR sandwich assay. Clin. Chim. Acta 259: 169–176.

O'Connor, T., Kane, M. M., and Gosling, J. P. (1995) The dependence of the detection limit of reagent-limited immunoassay on antibody affinity. Biochem. Soc. Trans. 23(2): 393S.

Pang, S. (1990) Nature 343: 85–89.

Peterson, E. T.; Blank, J.; Sprinzl, M.; Uhlenbeck, O. C. (1993). Selection for active *E. coli* tRNA(Phe) variants from a randomized library using two proteins. EMBO J. 12(7): 2950–2967.

Peterson, E. T.; Pan, T.; Coleman, J.; Uhlenbeck, O. C. (1994). In vitro selection of small RNAs that bind to *Escherichia coli* phenylalanyl-tRNA synthetase. J. Mol. Biol. 242(3): 186–192.

Piatak, M et al. (a) BioTechniques 14: 70–81; (b) Science 259: 1749–1754.

Pluckthun. (1994). *The Pharmacology of Monoclonal Antibodies*, vol. 113. Rosenburg and Moore eds. Springer-Verlag, New York, pp. 269–315.

Presta. (1992). *Curr. Op. Struct. Biol.* 2: 593–596.

Quinn, T. P.; Peters, K. G.; DeVries, C.; Ferrara, N.; Williams, L. T. (1993). Fetal liver kinase 1 is a receptor for vascular endothelial growth factor and is selectively expressed in vascular endothelium. Proc. Nat. Acad. Sci. U.S.A. 90(16): 7533–7537.

Raeymaekers, L. (1995) Genome Res. 5: 91–94.

Reichmann et al. (1988). *Nature,* 332: 323–329.

Renault et al. (1992). *Proc. Natl. Acad. Sci. USA,* 89: 5690–5694.

Ringquist, S.; Jones, T.; Snyder, E. E.; Gibson, T.; Boni, T.; Gold, L. (1995). High-affinity RNA ligands to *Escherichia coli* ribosomes and ribosomal protein S1: comparison of natural and unnatural binding sites. Biochemistry. 34(11): 3640–3648.

Ririe, K, Rasmussen, P. P., and Wittwer, C. T. (1977) Product differentiation by analysis of DNA melting curves during the polymerase chain reaction. Anal. Biochem. 245: 154–160.

Rose et al. (1991). *Proc. Natl. Acad. Sci. USA,* 88: 8641–8645.

Ruzicka, V. et al. (1993) Science 260: 698–699.

Saiki, R. K.; Gelfand, D. H.; Stoffel, S.; Scharf, S. J.; Higuchi, R.; Horn, G. T.; Mullis, K. B.; Erlich, H. A. (1988). Primer-directed enzymatic amplification of DNA with a thermostable DNA polymerase. Science. 239: 487491.

Saiki, R. K.; Scharf, S.; Faloona, F.; Mullis, K. B.; Horn, G. T.; Erlich, H. A.; Arnheim, N. 1985). Enzymatic amplification of β-globin genomic sequences and restriciton site analysis for diagnosis of sickle cell anemia. Science. 230: 1350–1354.

Sanna, P. P.; Weiss, F.; Samson, M. E.; Bloom, F. E.; Pich, E. M. (1995). Rapid induction of tumor necrosis factor α in the cerebrospinal fluid after intracerebroventricular injection of lipopolysaccharide revealed by a sensitive capture immuno-PCR assay. Proc. Natl. Acad. Sci. U.S.A. 92: 272–275.

Sano, T.; Smith, C. L.; Cantor, C. R. (1992). Immuno-PCR: very sensitive antigen detection by means of specific antibody-DNA conjugates. Science. 258: 120–122.

Sassanfar, M.; Szostak, J. (1993). An RNA motif that binds ATP. Nature. 364(6437): 550–553.

Schneider, D.; Gold, L.; Platt, T. (1993). Selective enrichment of RNA species for tight binding to *Escherichia coli* rho factor. FASEB J. 7(1): 201–207.

Schneider, D.; Tuerk, C.; Gold, L. (1992). Selection of high affinity RNA ligands to the bacteriophage R17 coat protein J. Mol. Biol. 228(3): 862–869.

Shweiki, D.; Itin, A.; Soffer, D.; Keshet, E. (1992). Vascular endothelial growth factor induced by hypoxia may mediate hypoxia-initiated angiogenesis. Nature. 259: 843–845.

Skoda, R. C. et al. (1993). *EMBO J.* 12: 2645–2653.

Souyri, M. et al. (1990). *Cell* 63: 1137.

Sperl, J.; Paliwal, V.; Ramabhadran, R.; Nowak, B.; Askenases, P. W. (1995). Soluble T cell receptors: detection and quantitative assay in fluid phase via ELISA or immuno-PCR. J. of Imm. Met. 186: 181–194.

Suzuki, A. (1995) Jpn. J. Cancer Res. 86: 885–889.

Szostak, J. W. (1992). In vitro genetics. TIBS. 17: 89–93.

Takaki et al. (1990). *EMBO J,* 9: 4367A374.

Takeshita et al. (1991). *Science,* 257: 379–382.

Tavernier et al. (1991). *Cell,* 66: 1175–1184.

Tijssen, P., Practice and Theory of Enzyme Immunoassays. in Laboratory Techniques in Biochemistry and Molecular Biology, vol. 15, ed. by Burdon, R. H. and van Knippenberg, P. H., Elsevier, N. Y., 1985, pp. 132–136.

Tischer, E.; Gospodarowicz, D.; Mitchell. R.; Silva, M.; Schilling, J.; Lau, K.; Crisp, T.; Fiddes, J. C.; Abraham, J. A. (1989). Vascular endothelial growth factor: a new member of the platelet-derived growth factor gene family. Bioch. & Bioph. Res. Comm. 165(3): 1198–1206.

Tsai, D. E.; Kenan, D. J.; Deene, J. D. (1992). In vitro selection of an RNA epitope immunologically cross-reactive with a peptide. Proc. Natl. Acad. Sci. U.S.A. 89(19): 8864–8868.

Tuerk, C.; Gold, L. (1990). Systematic evolution of ligands by exponential enrichment: RNA ligands to bacteriophage T4 DNA polymerase. Science. 249: 505–510.

Turek, C.; MacDougal-Waugh, S. (1993). In vitro evolution of functional nucleic acids: high-affinity RNA ligands of HIV-1 proteins. Gene. 137: 33–39.

Tyagi S., and Kramer FR. (1996) Molecular Beacons: Probes that fluoresce upon hybridization. Nature Biotechnology 14(3): 303–308.

Vaisman, N.; Gospodarowicz, D.; Neufled, G. (1990). Characterization of the receptors for vascular endothelial growth factor. J. of Biol. Chem. 265(32): 19461–19466.

Vigon, I. et al. (1992). *Proc. Natl. Acad. Sci.* 89: 5640.

Waltenberger, J.; Claesson-Welsh, L.; Siegbahn, A.; Shibuya, M.; Heldin, C. H. (1994). Different signal transduction properties of KDR and flt-1, two rectoptors for vascular endothelial growth factor. J. of Biol. Chem. 269(43): 26988–26995.

Wiegand, T. W.; Williams, P. B.; Dreskin, S. C.; Jouvin, M.; Kinet, J.; Tasset, D. (1996). High-affinity oligonucleotide ligands to human IgE inhibit binding to FcE receptor I. J. of Imm. 157(1): 221–230.

Williams, S.; Schwer, C.; Kirshnarao, A.; Heid, C.; Karger, B.; Williams, P. M. (1996). Quantitative competitive PCR: Analysis of amplified products of the HIV-1 gag gene by capillary electrophoresis with laser induced fluorescence detection. Anal. Bioch. 236(1): 145–152.

Wittwer, C., Herrmann, M., Moss, A., and Rasmussen, R. (1977) Continuous fluorescence monitoring of rapid cycle DNA amplification. BioTechniques 22(1): 130–138;

Wittwer, C., Ririe, K., Andrew, R., David, D., Gundry, R., and Balis, U. (1997) The LightCycler(™): A microvolume multisample fluorimeter with rapid temperature control. BioTechniques 22(1): 176–181.

Wyatt, J. R.; Pulglisi, J. D., Tinoco, I. (1989). RNA folding: psuedoknots, loops and bulges. BioEssays. 11(4): 100–106.

Yamasaki et al. (1988). *Science,* 241: 825–828.

Zapata et al. (1995). *Protein Eng.* 8(10): 1057–1062.

Zhou, H.; Fisher, R. J.; Papas, T. S. (1993). Universal immuno-PCR for ultra-sensitive traget protein detection. Nuc. Acids Res. 21(25): 6038–6039.

Zuker, M. (1989). On Finding All Suboptimal Foldings of an RNA Molecule. Science. 244: 48–52.

What is claimed is:

1. A method for quantitating or detecting the presence of a target molecule in a sample which contains the target molecule and a nuclease, comprising:
   (a) exposing the sample to a capture antibody or target molecule binding fragment thereof of which binds to the target molecule under conditions whereby a capture antibody:target molecule or a target molecule binding fragment:target molecule complex is formed;
   (b) adding to the complex from step (a), an RNA or DNA aptamer detector molecule which binds to the target molecule to form a capture antibody:target molecule:aptamer or a target molecule binding fragment::target molecule:aptamer ternary complex;
   (c) washing the complex from step (a) or (b) or both to remove said nuclease;
   (d) when the aptamer is an RNA detector molecule, reverse transcribing the RNA to DNA;
   (e) amplifying the DNA aptamer or DNA obtained by step (d) by PCR amplification; and
   (f) quantitating or detecting the PCR amplified DNA using a detectable non-primer probe which binds to the DNA using real time PCR during PCR amplification;
   wherein quantitating or detecting the PCR amplified DNA quantitates or detects the target molecule.

2. The method of claim 1, further comprising washing the capture antibody:target molecule complex to remove unbound sample after step (a).

3. The method of claim 1, wherein the capture antibody is bound to a solid support or carrier during step (a) or (b).

4. The method of claim 3, wherein the solid support is a PCR tube.

5. The method of claim 1, wherein the capture antibody is in solution during step (a) or (b).

6. The method of claim 5, wherein the capture antibody is labeled with biotin and is bound to a streptavidin or avidin labeled support.

7. The method of claim 1, wherein the target molecule is an organic compound having a molecular weight of about 100 to about 1000 grams/mole.

8. The method of claim 1, wherein the target molecule is a protein or fragment thereof.

9. The method of claim 8, wherein the protein is a cytokine selected from the group consisting of growth hormone, insulin-like growth factors, human growth hormone, N-methionyl human growth hormone, bovine growth hormone, parathyroid hormone, thyroxine, insulin, proinsulin, relaxin, prorelaxin, glycoprotein hormones, follicle stimulating hormone (FSH), thyroid stimulating hormone (TSH), leutinizing hormone (LH), hematopoietic growth factor, vesicular endothelial growth factor (VEGF), hepatic growth factor, fibroblast growth factor, prolactin, placental lactogen, tumor necrosis factor-alpha, tumor necrosis factor-beta, mullerian-inhibiting substance, mouse gonadotropin-associated peptide, inhibin, activin vascular endothelial growth factor, integrin, nerve growth factors (NGFs), NGF-beta, platelet-growth factor, transforming growth factors (TGFs), TGF-alpha, TGF-beta, insulin-like growth factor-I, insulin-like growth factor-II, erythropoietin (EPO), osteoinductive factors, interferons, interferon-alpha, interferon-beta, interferon-gamma, colony stimulating factors (CSFs), macrophage-CSF (M-CSF), granulocyte-macrophage-CSF (GM-CSF), granulocyte-CSF (G-CSF), thrombopoietin (TPO), interleukins (ILs), IL-1, IL-1 alpha, IL-2, IL-3, IL-4, IL-5, IL-6, IL-7, IL-8, IL-9, IL-11, IL-12, LIF, SCF, neurturin (NTN) and kit-ligand (KL).

10. The method of claim 1, wherein the sample is selected from the group consisting of blood, serum, sputum, urine, semen, cerebrospinal fluid, bronchial aspirate and organ tissue.

11. The method of claim 1, wherein the detectable non-primer probe comprises a nucleic acid having a fluorescent dye label.

12. The method of claim 11, wherein the fluorescent dye label comprises two dyes, a reporter dye and a quencher dye, which fluoresce at different wavelengths.

13. The method of claim 1, wherein the nucleic acid detector molecule is RNA and the RNA detector molecule is reverse transcribed to form DNA before or during amplifying step d.

14. The method of claim 1, wherein the RNA detector molecule is reversed transcribed at a temperature sufficient to dissociate the detector molecule from the capture antibody:target molecule:aptamer ternary complex and reverse transcribe the RNA.

15. The method of claim 14, wherein the temperature is about 50 C to about 70 C.

16. The method of claim 1, wherein said quantitating or detecting the PCR amplified DNA quantitates or detects the target molecule when present at a concentration equal to or less than 1000 pg/mL.

17. The method of claim 16, wherein said quantitating or detecting the PCR amplified DNA quantitates or detects the target molecule when present at a concentration equal to or less than 100 pg/mL.

18. The method of claim 17, wherein said quantitating or detecting the PCR amplified DNA quantitates or detects the target molecule when present at a concentration equal to or less than 1 pg/mL.

19. The method of claim 1, wherein said quantitating or detecting the PCR amplified DNA quantitates or detects the target molecule when present at a concentration of about 100 to about 5000 pg/mL.

20. The method of claim 19, wherein said quantitating or detecting the PCR amplified DNA quantitates or detects the target molecule when present at a concentration of about 100 to about 1000 pg/mL.

21. The method of claim 19, wherein said quantitating or detecting the PCR amplified DNA quantitates or detects the target molecule when present at a concentration of about 1000 to about 5000 pg/mL.

22. The method of claim 1, wherein said quantitating or detecting the PCR amplified DNA quantitates or detects the target molecule when present at a concentration of about 3 to about 5000 pg/mL.

23. The method of claim 22, wherein said quantitating or detecting the PCR amplified DNA quantitates or detects the target molecule when present at a concentration of about 3 to about 1000 pg/mL.

24. The method of claim 22, wherein said quantitating or detecting the PCR amplified DNA quantitates or detects the target molecule when present at a concentration of about 3 to about 100 pg/mL.

25. The method of claim 1, wherein said quantitating or detecting the PCR amplified DNA quantitates or detects the target molecule when present at a concentration of about 0.4 to about 5000 pg/mL.

26. The method of claim 25, wherein said quantitating or detecting the PCR amplified DNA quantitates or detects the target molecule when present at a concentration of about 0.4 to about 1000 pg/mL.

27. The method of claim 26, wherein said quantitating or detecting the PCR amplified DNA quantities or detects the target molecule when present at a concentration of about 0.4 to about 100 pg/mL.

28. The method of claim 1, wherein said quantitating or detecting the PCR amplified DNA quantitates or detects the target molecule when present at a concentration of about 1 to about 5000 pg/mL.

29. The method of claim 28, wherein said quantitating or detecting the PCR amplified DNA quantitates or detects the target molecule when present at a concentration of about 1 to about 1000 pg/mL.

30. The method of claim 29, wherein said quantitating or detecting the PCR amplified DNA quantitates or detects the target molecule when present at a concentration of about 1 to about 100 pg/mL.

31. The method of claim 1, wherein said quantitating or detecting the PCR amplified DNA quantitates or detects the target molecule when present at a concentration of about 0.03 to about 5000 pg/mL.

32. The method of claim 31, wherein said quantitating or detecting the PCR amplified DNA quantitates or detects the target molecule when present at a concentration of about 0.03 to about 1000 pg/mL.

33. The method of claim 32, wherein said quantitating or detecting the PCR amplified DNA quantitates or detects the target molecule when present at a concentration of about 0.03 to about 100 pg/mL.

34. The method of claim 1, wherein said quantitating or detecting the PCR amplified DNA quantities or detects the target molecule when present at a concentration of about 0.005 to about 5000 pg/mL.

35. The method of claim 34, wherein said quantities or detecting the PCR amplified DNA quantities or detects the target molecule when present at a concentration of about 0.005 to about 1000 pg/mL.

36. The method of claim 35, wherein said quantitating or detecting the PCR amplified DNA quantitates or detects the target molecule when present at a concentration of about 0.005 to about 100 pg/mL.

37. The method of claim 36, wherein said quantitating or detecting the PCR amplified DNA quantitates or detects the target molecule when present at a concentration of about 0.005 to about 1 pg/mL.

38. A method for quantitating or detecting the presence of a target molecule in a biological sample which contains the target molecule and a nuclease, comprising:

(a) exposing the sample to a capture antibody or target molecule binding fragment thereof which binds to the target molecule under conditions whereby a capture antibody:target molecule or a target molecule binding fragment:target molecule complex is formed;

(b) adding to the complex from step (a), an RNA or DNA aptamer detector molecule which binds to the target molecule to form a capture antibody:target molecule:aptamer or a target molecule binding fragment::target molecule:aptamer ternary complex;

(c) washing the complex from step (a) or (b) or both to remove said nuclease;

(d) when the aptamer is an RNA detector molecule, revere transcribing the RNA to DNA;

(e) amplifying the DNA aptamer or DNA obtained by step (d) by PCR amplification; and (f) quantitating or detecting the PCR amplified DNA using a detectable non-primer probe which binds to the DNA using real time PCR during PCR amplification;

wherein quantitating or detecting the PCR amplified DNA quantitates or detects the target molecule when present at a concentration of about 0.005 to about 5000 pg/mL.

39. The method of claim 38, further comprising washing the capture antibody:target molecule complex to remove unbound sample after step (a).

40. The method of claim 38, wherein the capture antibody is bound to a solid support or carrier during step (a) or (b).

41. The method of claim 40, wherein the solid support is a PCR tube.

42. The method of claim 41, wherein said quantitating or detecting the PCR amplified DNA quantitates or detects the target molecule when present at a concentration equal to or less than 100 pg/mL.

43. The method of claim 42, wherein said quantitating or detecting the PCR amplified DNA quantitates or detects the target molecule when present at a concentration equal to or less than 1 pg/mL.

44. The method of claim 38, wherein the capture antibody is in solution during step (a) or (b).

45. The method of claim 44, wherein the capture antibody is labeled with biotin and is bound to a streptavidin or avidin labeled support.

46. The method of claim 38, wherein the target molecule is a protein or fragment thereof.

47. The method of claim 46, wherein the protein is a cytokine selected from the group consisting of growth hormone, insulin-like growth factors, human growth hormone, N-methionyl human growth hormone, bovine growth hormone, parathyroid hormone, thyroxine, insulin, proinsulin, relaxin, prorelaxin, glycoprotein hormones, follicle stimulating hormone (FSH), thyroid stimulating hormone (TSH), leutinizing hormone (LH), hematopoietic growth factor, vesicular endothelial growth factor (VEGF), hepatic growth factor, fibroblast growth factor, prolactin, placental lactogen, tumor necrosis factor-alpha, tumor necrosis factor-beta, mullerian-inhibiting substance, mouse gonadotropin-associated peptide, inhibin, activin, vascular endothelial growth factor, integrin, nerve growth factors (NGFs), NGF-beta, platelet-growth factor, transforming growth factors (TGFs), TGF-alpha, TGF-beta, insulin-like growth factor-I, insulin-like growth factor-II, erythropoietin (EPO), osteoinductive factors, interferons, interferon-alpha, interferon-beta, interferon-gamma, colony stimulating factors (CSFs), macrophage-CSF (M-CSF), granulocyte-macrophage-CSF (GM-CSF), granulocyte-CSF (G-CSF), thrombopoietin (TPO), interleukins (ILs), IL-1, IL-1 alpha, IL-2, IL-3, IL-4, IL-5, IL-6, IL-7, IL-8, IL-9, IL-11, IL-12, LIF, SCF, neurturin (NTN) and kit-ligand (KL).

48. The method of claim 38, wherein the sample is selected from the group consisting of blood, serum, urine, semen, cerebrospinal fluid, bronchial aspirate and organ tissue.

49. The method of claim 38, wherein the detectable non-primer probe comprises a nucleic acid having a fluorescent dye label.

50. The method of claim 49, wherein the fluorescent dye label comprises two dyes, a reporter dye and a quencher dye, which fluorescent at different wavelengths.

51. The method of claim 38, wherein the nucleic acid detector molecule is RNA and the RNA detector molecule is reverse transcribed to form DNA before or during amplifying step d.

52. The method of claim 38, wherein the RNA detector molecule is reversed transcribed at a temperature sufficient to dissociate the detector molecule from the capture antibody:target molecule:aptamer ternary complex and reverse transcribe the RNA.

53. The method of claim 52, wherein the temperature is about 50 C to about 70 C.

54. The method of claim 38, wherein said quantitating or detecting the PCR amplified DNA quantitates or detects the target molecule when present at a concentration equal to or less than 1000 pg/mL.

55. The method of claim 38, wherein said quantitating or detecting the PCR amplified DNA quantitates or detects the target molecule when present at a concentration of about 100 to about 5000 pg/mL.

56. The method of claim 38, wherein said quantitating or detecting the PCR amplified DNA quantitates or detects the target molecule when present at a concentration of about 3 to about 5000 pg/mL.

57. The method of claim 38, wherein said quantitating or detecting the PCR amplified DNA quantitates or detects the target molecule when present at a concentration of about 0.4 to about 5000 pg/mL.

58. The method of claim 38, wherein said quantitating or detecting the PCR amplified DNA quantitates or detects the target molecule when present at a concentration of about 0.03 to about 5000 pg/mL.

59. The method of claim 58, wherein said quantitating or detecting the PCR amplified DNA quantitates or detects the target molecule when present at a concentration of about 0.03 to about 1000 pg/mL.

60. The method of claim 59, wherein said quantitating or detecting the PCR amplified DNA quantitates or detects the target molecule when present at a concentration of about 0.03 to about 100 pg/mL.

\* \* \* \* \*

UNITED STATES PATENT AND TRADEMARK OFFICE
CERTIFICATE OF CORRECTION

PATENT NO.    : 6,927,024 B2
DATED         : August 9, 2005
INVENTOR(S)   : Dodge et al.

It is certified that error appears in the above-identified patent and that said Letters Patent is hereby corrected as shown below:

Title page,
Item [56], References Cited, OTHER PUBLICATIONS,
"Hendrickson et al." reference, "covalent DNa-labeled natibodies and" should read -- covalent DNA-labeled antibodies and --.
"Ellington and Szostak" refererence, "the bind specific ligands" *Nature*" should read -- that bind specific ligands" *Nature* --.
"Ferre" reference: "of semi-quantitative" should read -- or semi-quantitative --.

Column 9,
Line 24, "antibody Kd (1 µg/ml for the" should read -- antibody Kd (1 pg/ml for the --.

Column 12,
Line 36, "IL-5 (Takakiet al., 1990);" should read -- IL-5 (Takaki et al., 1990); --.

Column 24,
Line 7, "Mat (Coming Costar)" should read -- Mat (Corning Costar) --.

Column 25,
Lines 66-67, "(see above) bring the volume to bring the volume to 10 µl." should read -- (see above) and water to bring the volume to 10 µl. --.

Column 26,
Line 45, "down to 0.03 pg/mL" should read -- down to 0.031 pg/mL --.

Column 27,
Line 18, "CTTTTCGTTGGATGTATCTGCGGCGTTT" should read -- CTTTCGTTGGATGTATCTGCGGCGTTT --.

Column 28,
Line 22, "50 el/well of" should read -- 50 µl/well of --.

Column 29,
Line 12, "Andrake, M.; Guild, M.;" should read -- Andrake, M.; Guild, N.; --.

Column 30,
Line 40, "that mimes a major" should read -- that mimics a major --.

Column 31,
Line 11, "Gibson et al. (I 996)." should read -- Gibson et al. (1996). --.

UNITED STATES PATENT AND TRADEMARK OFFICE
CERTIFICATE OF CORRECTION

PATENT NO. : 6,927,024 B2
DATED : August 9, 2005
INVENTOR(S) : Dodge et al.

It is certified that error appears in the above-identified patent and that said Letters Patent is hereby corrected as shown below:

Column 33,
Line 48, "Gibson, T.; Boni, T.;" should read -- Gibson, T.; Boni, I.; --.
Line 61, "Higuchi, R.; Hom, G. T.;" should read -- Higuchi, R.; Horn, G. T.; --.
Line 64, "487491." should read -- 487-491. --.
Line 65, "Mullis, K. B.; Hom, G." should read -- Mullis, K. B.; Horn, G. --.

Column 47,
Line 13, "inhibin, activan vascular" should read -- inhibin, activin, vascular --.

Column 48,
Line 50, "DNA quantities or detects" should read -- DNA quantitates or detects --.
Lines 53-54, "said quantities or detecting the PCR amplified DNA quantities or detects" should read -- said quantitating or detecting the PCR amplified DNA quantitates or detects --.

Column 49,
Line 13, "detector molecule, revere" should read -- detector molecule, reverse --.

Column 50,
Line 11, "blood, serum, urine," should read -- blood, serum, sputum, urine, --.
Line 19, "which fluorescent at" should read -- which fluoresce at --.

Signed and Sealed this

Twenty-first Day of March, 2006

JON W. DUDAS
*Director of the United States Patent and Trademark Office*